(12) United States Patent
Stief

(10) Patent No.: US 7,192,697 B2
(45) Date of Patent: Mar. 20, 2007

(54) PROCEDURE FOR ANTI-LIMULUS-FACTORS-INDEPENDENT DETERMINATION OF LIPOPOLYSACCHARIDE- AND/OR LIPID-A- AND/OR GLUCAN- REACTIVITY, SUITABLE TEST SYSTEM FOR THIS AS WELL AS ITS USAGE

(76) Inventor: Thomas W. Stief, Limessor. 15, Pohlheim (DE) 35415

( * ) Notice: Subject to any disclaimer, the term of this patent is extended or adjusted under 35 U.S.C. 154(b) by 0 days.

(21) Appl. No.: 11/137,612

(22) Filed: May 25, 2005

(65) Prior Publication Data

US 2005/0266514 A1 Dec. 1, 2005

(30) Foreign Application Priority Data

May 26, 2004 (DE) .................... 10 2004 025 780

(51) Int. Cl.
C12Q 1/00 (2006.01)
G01N 1/00 (2006.01)
(52) U.S. Cl. .......................................... 435/4; 436/175
(58) Field of Classification Search .................... 435/4, 435/810, 23, 24, 175; 436/175
See application file for complete search history.

(56) References Cited

U.S. PATENT DOCUMENTS

| | | | |
|---|---|---|---|
| 3,954,663 A | 5/1976 | Yamamoto et al. | |
| 4,495,294 A | 1/1985 | Nakahara et al. | |
| 5,057,414 A | 10/1991 | Stief | |
| 6,384,200 B1 * | 5/2002 | Wainwright et al. | 530/412 |

FOREIGN PATENT DOCUMENTS

| DE | 195 49 117 A1 | 7/1997 |
|---|---|---|
| EP | 0 297 597 | 1/1989 |
| EP | 0 569 033 | 11/1993 |
| EP | 0 906 574 | 4/1999 |

OTHER PUBLICATIONS

Moraga et al. Activation of Primary Human Monocytes by the Oxidized Form of Alpha1-Antitrypsin; The Journal of Biological Chemistry, vol. 275, No. 11 (2000) pp. 7693-7700.*

Stief et al. Singlet Oxygen Inactivates Fibrinogen, Factor V, Factor VIII, Factor X and Platelet Aggregation of Human Blood; Thrombosis Research, vol. 97 (2000) pp. 473-480.*

Abstract of Stief, T. W. et al., "Inactivation of Serine Proteinase Inhibitors (Serpins) in Human Plasma By Reactive Oxidants," Biol Chem Hoppe Seyler, Dec. 1988, 369 (12): 1337-42; abstract from PubMed, www.ncbi.nlm.nih.gov.

Abstract of Stief, T.W. et al., "Singlet Oxygen ((1)O2) Inactivates Plasmatic Free and Complexed Alpha2-Macroglobulin," Thromb. Res., Jun. 15, 2000; 98 (6), pp. 541-547; abstract from PubMed, www.ncbi.nlm.nih.gov.

Hurley, J. C., "Endotoxemia: Methods of Detection and Clinical Correlates", Clinical Microbiology Reviews (Apr. 1995), vol. 8, No. 2, pp. 268-292.

Tsuji, K. et al. Recovery of endotoxin from human plasma by acid oxidative treatments as monitored by an automated microtiter plate-chromogenic substrate limulus amebocyte lysate (LAL) assay. Progress in Clinical and Biological Research. In *Detection of Bacterial Endotoxins with the Limulus Amebocyte Lysate Test*, New York: Alan R. Liss, Inc., 1987, 443-457.

Hurley, J.C. Endotoxemia: Methods of Detection and Clinical Correlates. Clinical Microbiology Reviews, 8(2), 1995, 268-292.

Obayashi, T. Addition of perchloric acid to blood samples for colorimetric limulus test using chromogenic substrate: Comparison with conventional procedures and clinical applications. Journal of Laboratory and Clinical Medicine, 104(3), 1984, 321-330.

Ochiai, M. et al. A Limulus Amoebocyte Lysate Activating Activity (LAL Activity) that Lacks Biological Activities of Endotoxin Found in Biological Products. Microbiol. Immunol. 46(8), 2002, 527-533.

* cited by examiner

*Primary Examiner*—Jon Weber
*Assistant Examiner*—Paul C. Martin
(74) *Attorney, Agent, or Firm*—Connolly Bove Lodge & Hutz LLP

(57) ABSTRACT

A modified limulus test procedure is provided to measure the lipopolysaccharide (LPS), lipid A, and/or glucan reactivity in a biological liquid. The test procedure is independent of the anti-limulus factors present in the sample. The procedure involves strong oxidative treatment of the biological liquid sample.

14 Claims, 15 Drawing Sheets

Legend as in Abb. 3

Figure 1:
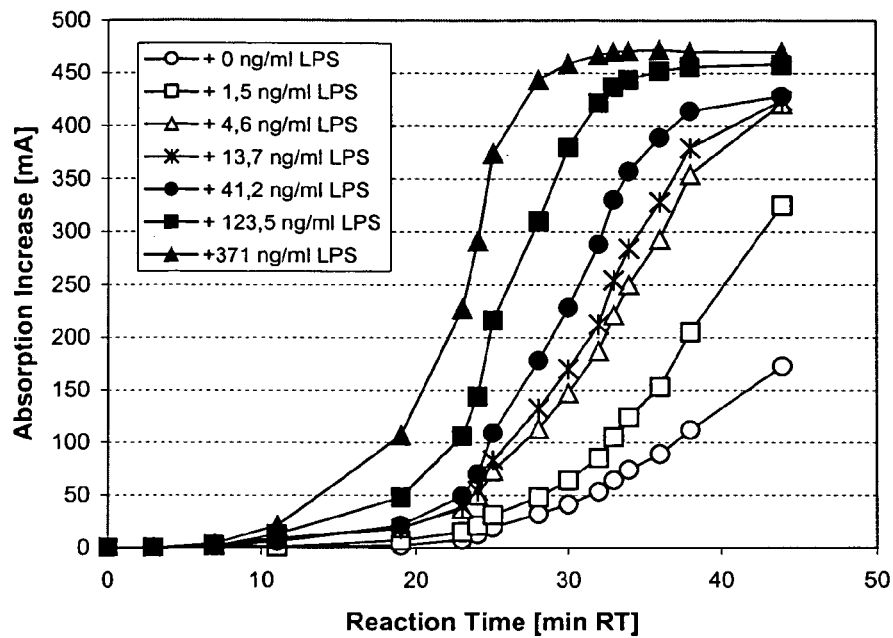

PROCEDURE FOR ANTI-LIMULUS-FACTORS-INDEPENDENT DETERMINATION OF LIPOPOLYSACCHARIDE- AND/OR LIPID-A- AND/OR GLUCAN- REACTIVITY, SUITABLE TEST SYSTEM FOR THIS AS WELL AS ITS USAGE

Procedure for anti-*Limulus*-factors-independent determination of lipopolysaccharide- and/or lipid-A- and/or glucan-reactivity, suitable test system for this as well as its usage.

BACKGROUND OF THE INVENTION

1. Field of the Invention

The present invention concerns an improved test to determine the lipopolysaccharide- and/or lipid-A- and/or glucan-reactivity in body fluids, a suitable test system for this as well as its usage to determine lipopolysaccharide- and/or glucan-reactivity.

By reactivity is understood in the context of this description the activity of lipopolysaccharide and/or lipid-A and/or glucan, particularly beta-1,3-D-glucan, in a biological liquid as for example plasma. Reactive lipopolysaccharide and/or lipid-A and/or glucan is pathophysiologically and/or pharmacologically-toxicologically active and/or free lipopolysaccharide and/or lipid-A and/or glucan.

2. Description of Related Art

Infections with gram-negative bacteria (as *Escherichia coli*) or with funghi (as *Candida albicans*) represent a great medical problem since a long time. The germinates can invade into the blood stream or into the meningeal space where they can cause life threatening conditions, as sepsis or meningitis. Therefore these medically so relevant pathogens should be diagnosed as soon as possible.

However, microbiological procedures to grow these germinates are very time consuming. In many cases the diagnosis can be made not until days or weeks. However, in few hours the clinical condition of the patient can worsen in such a way, that in the worst case he dies due to this infection.

Therefore, it was not missing on to try to shorten the time interval to make a diagnosis. One of theses approaches is the detection of lipopolysaccharides (in the following termed "LPS"), of lipid-A or of glucans with the so called *Limulus*-Assay. LPS, lipid-A and glucans are dangerous for the patient, because their presence in blood can cause a pathologic disseminated intravascular coagulation (DIC).

The cell wall of gram-negative bacteria partly consists of LPS (formely called endotoxin), which is composed of a harmless polysaccharide part and a for many cells dangerous lipid-A part.

The LPS- and/or lipid-A- and/or glucan-reactivity is of high pathophysiological importance: active LPS and/or free LPS, and/or active glucan and/or free glucan reacts for example very intensively with the monocytes of blood or with the endothelium.

The monocytes can thereby be activated very strongly or can be destroyed, and internal cell compartments get in contact with plasma and thrombocytes.

Since monocytes contain DNA and so-called tissue-factor, the coagulation in sepsis is activated immediately. A life-threateningly enhanced disseminated intravascular coagulation results with e.g. multiple thromboses in small vessels, that can result into multi-organ-failure.

With the present invention a procedure is made available, that imitates the pathophysiological interaction, i.e. the reactivity, of LPS, lipid-A, glucan, respectively, with susceptible cells, whereby the cells and/or cell membranes are substituted in vitro by the *Limulus*-factors. Therefore, one such procedure that detects sensitively and specifically within minutes LPS, lipid-A or glucans, particularly reactive and/or free LPS and/or reactive and/or free lipid-A and/or reactive and/or free glucans, is of great clinical importance.

According to the state of the art LPS is detected with the *Limulus*-assay [Hurley J. C. Endotoxemia: methods of detection and clinical correlates. Clinical Microbiology Reviews 1995; 8: 268–292]. The principle of this test is that LPS—but also glucans—activate the coagulogen/coagulin system of the Horseshoe-crab (*Limulus polyphemus*) called the *Limulus*-system.

The *Limulus*-system is a defense system of the horseshoe-crab against invading pathological germinates and represents a primitive system of native immunity.

The *limulus*-system mainly consists of the following factors: factor C, factor B, factor A and coagulogen.

LPS or lipid-A activates factor C, activated factor C activates factor B, activated factor B activates factor A. Activated Factor A converts soluble coagulogen into insolulbe coagulin.

In the *Limulus*-system for glucans, that are components of funghi, there is also a factor G, that is activated by glucans, particularly beta-1,3-D-glucans, to a serine protease, whereby activated factor A is formed.

In the *Limulus*-assay LPS and/or lipid-A and/or glucans of the sample act on *Limulus* amebocyte-factors, in the following called *Limulus*-factors, and results into changes, that can be detected in different ways. These *Limulus*-factors are prepared according to the state of the art from the lysate of *Limulus*-amebocytes, wherefrom the abbreviation LAL comes.

Examples for detection procedures are the LAL-gelation test, the coagulogen-based LAL assay and the chromogenic LAL assay (see Hurley J. C., Clinical Microbiology Reviews 1995; 8: 272).

In the chromogenic LAL assay or the chromogenic *Limulus*-test the reaction of the activated Factor A on coagulogen is imitated by substitution of coagulogen by a chromogenic substrate, e.g. S-2834® (Isoleucyl-Glutamyl-Glycyl-Arginyl-paranitro-Anilide=Ile-Glu-Gly-Arg-pNA) or S-2423® (CH3-CO-Ile-Glu-Gly-Arg-pNA) (Chromogenix, Mölndal, Sweden).

The chromogenic *Limulus*-test is commercially available, e.g. under the trade names *Limulus* Amebocyte Lysate Endochrome® (Charles River Endosafe; Charleston, USA), Coatest® Plasma Endotoxin or Coamatic® Endotoxin (Chromogenix, Mölndal, Sweden) or Pyrochrome® (Cape Code, Falmouth, USA).

Usually the chromogenic *Limulus*-test is performed in the so-called end Hyperbolic-Rate-Assay-Kinetic (at 37° C., incubation time=41 min for plasma, product information of Pyrochrome®, Haemochrom, Essen, Germany) i.e. chromogenic substrate and the *Limulus*-Factors C, B, A are added together to the sample to be tested for endotoxin. Consequently, the activation of the factors C, B, A and the cleavage of the substrate happens at the same time. The longer the assay incubation time is prior to addition of the stop reagent, the more activated factor A is generated and the more chromogenic substrate is cleaved.

Figure 21:
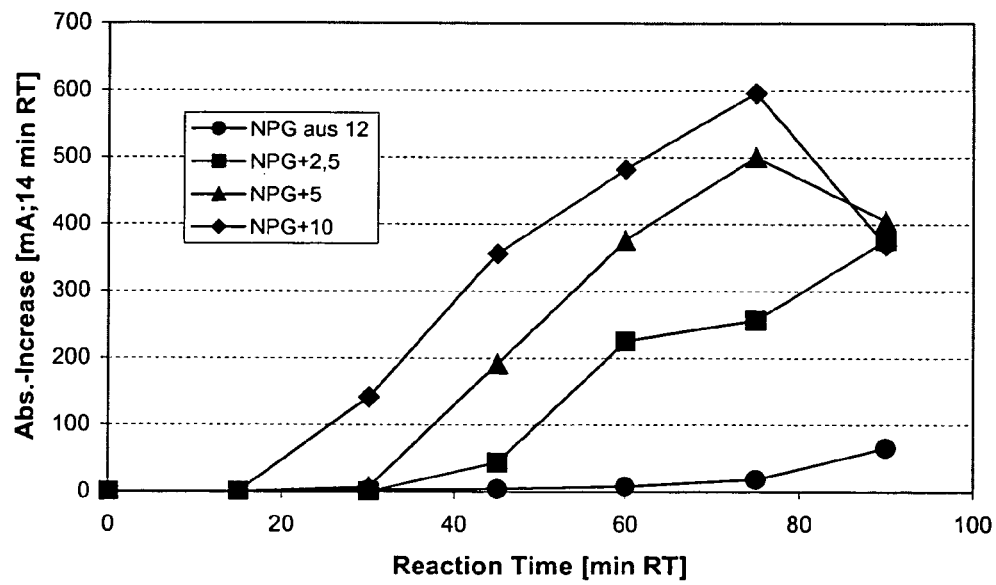

Alternatively, the chromogenic substrate can be added not until a time interval after addition of the factors C, B, A. The disadvantage of this is that during the action of the endotoxin on the factors C, B, and A increasingly autocatalytic and/or autodestructive interactions happen (s. FIG. 21). The chromogenic substrate (as added in the Hyperbolic-Rate-Assay) inhibits partially these interactions.

The main-problem with the *Limulus*-test is, that anti-*Limulus* factors of the sample, as for example proteins, especially serine protease-inhibitors, as antithrombin III and/or heparin cofaktor II and/or alpha2-antiplasmin, disturb the activation of the *Limulus*-system. This means that the result of the *Limulus*-test depends among other things on the content of anti-*Limulus* factors in the sample, as e.g. proteins, especially serine protease-inhibitors as antithrombin III and/or heparin cofaktor II and/or alpha2-antiplasmin (see FIGS. 12, 14).

This interference is eliminated according to the state of the art by 10 fold dilution of the sample and by heating the diluted sample for 15–20 min at 75° C. prior to the *Limulus*-test. Optionally the sample may be strong acidified for inactivating anti-*Limulus* factors (see Obayashi, T. et al. Clin. Chim. Acta 149, 55–65, 1985; J. Lab. Clin Med. 4, 321–330, 1984; U.S. Pat. No. 4,495,294). However, this procedure is problematic, because LPS and/or lipid-A and/or glucans that had been bound to physiologic inhibitors and is hence inactive can be released from the binding, i.e. the method does not mainly measure reactive and/or active and/or free but also bound LPS or lipid-A or glucan, respectively, with the consequence that this method is not routine-suited. Inhibited LPS, lipid-A, or glucan, respectively, has subordinate pathophyiological importance. Additionally, the active or free LPS or lipid-A molecules of the sample are nearly completely inactivated by heat treatment. The commercially available *Limulus*-tests have not found entrance into the clinical routine among other things due to these problems.

For example there are plasmatic antibodies and other binding-proteins, as the Lipopolysaccharide-Binding-Protein (LBP), that neutralize LPS and/or lipid-A and/or glucans. However, this bound and thereby neutralized LPS and/or lipid-A and/or glucan is of subordinate clinical importance. Of pathophysiologic importance is LPS, lipid-A or glucan (as e.g. the *Candida*-substance zymosan A), that is not-neutralized and/or free, the so-called reactive LPS or lipid-A or glucan, respectively, and can therefore react freely with susceptible cells as e.g. the monocytes of the blood. Releasing this neutralized LPS and/or lipid-A and/or glucan e.g. by heat pretreatment would falsificate the test result and would allow only a limited conclusion about the concentration of the not-neutralized LPS and/or lipid-A and/or glucan.

Basing on this state of the art the task of the present invention was to find a simple procedure and a corresponding suitable test system that allows to determine rapidly the content of active LPS and/or active lipid-A and/or active glucan of a sample, i.e. the LPS-reactivity and/or lipid-A reactivity and/or glucan reactivity.

A further task of the present invention was to find a procedure and a suitable test system that allows to differentiate active LPS or active lipid-A, respectively, from active glucan of a sample.

A further task of the present invention was to find a procedure and a suitable test system that allows to determine the active and/or free LPS and/or lipid-A and/or glucan of a sample and that is insensitive to neutralized LPS and/or lipid-A and/or glucan.

A still further task of the present invention was to find a procedure and a suitable test system operating with a linear kinetic and/or that is routine suitable.

A still further task of the present invention was to find a suitable test system that allows to omit the prior dilution and/or heat treatment of the sample to determine LPS and/or lipid-A and/or glucan.

Surprisingly it showed up that by addition of a suitable oxidant, if appropriate together with a detergent, such as e.g. Triton-X100®, preferably in a final concentration of up to 0,1%, and/or a solution mediator, as e.g. polyethylene glycol, preferably in a final concentration of up to 10%, the interference of the matrix of the sample (=surrounding of the parameter to be tested for) the disturbing factors on the *Limulus*-system could be eliminated.

Although it is known from EP-A-297,597, that by oxidative treatment of biological liquids the activity of serine proteases or of serine protease inhibitors can be determined, however this document does not refers to the usage of oxidants in the *Limulus*-assay. Additionally, according to the present invention it turned out that for the usage with the *Limulus*-system substantially higher oxidant doses are necessary that are e.g. 5–10 fold over the dose that are necessary to inactivate oxidant-sensible serine protease inhibitors.

BRIEF SUMMARY OF THE INVENTION

The present invention relates to a procedure to determine the content of lipopolysaccharide and/or lipid-A and/or glucan in biological liquids comprising
a) Treatment of the sample with at least one oxidant,
b) Addition of at least one *Limulus* amebocyte—factor to the oxidized sample, and
c) Determination of the activation of at least one of the *Limulus* amebocyte—factors.

DETAILED DESCRIPTION OF THE INVENTION

Oxidants according to the invention can be of arbitrary nature, so far they oxidize the anti-*Limulus* factors of the sample, especially antithrombin III and/or heparin cofactor II and/or alpha2-antiplasmin.

Examples for oxidants are halogen-amides, halogen-imides and halogen-hydroxyles including the salts of these compounds, inorganic und organic peroxides, such as hydrogen peroxide or cumylhydroperoxide, inorganic and organic per-acids, such as peroxomonosulfuric acid, peroxodisulfuric acid, perchloric acid, peroxoacetic acid, or the salts of these acids, singlet oxygen ($^1O_2$)-generators such as chloramines or salts of HOCl, particularly chloramine-T® (N-chlor-toluol-sulfonamide) or chloramine-B® (N-chlor-benzol-sulfonamide), or further agents, that contain positive halogen, such as N-brom-succinimide, N-chlorsuccinimide, 2,4,6-tribromo-4-methylcyclo-hexadienone, BNPS-skatole, t-butylhypochlorite, trichlormethane sulfonyl-chloride, 1-chlorobenzotriazole, iodobenzoldichloride in aqueous pyridine, pyridine-bromide-complexes, quinolines and 1,4-diazobicyclo[2.2.2]octane in aqueous acetic acid or dye-mediated photooxidizers (e.g. methyleneblue, eosin, riboflavin, hematoporphyrin).

Preferably used oxidants are nonradical oxidants, particularly singlet-oxygen-generators, especially preferred the singlet-oxygen ($^1O_2$)-generators chloramine, as e.g. chloramine-T® (N-chlor-toluol-sulfonamide).

The according to the invention used oxidants are added in relatively high doses to inactivate the anti-*Limulus* factors, however without changing the reactivity of LPS and/or glucan; particularly in the assay-procedure it must be avoided to reactivate or to release out of the binding inactive and/or bound LPS and/or glucan of the sample and not to inactivate active LPS and/or lipid-A and/or glucan.

Oxidant doses are typically necessary, that are more than 5–10 fold above the doses that are necessary in plasma for the oxidative inactivation of oxidant-sensible serine protease inhibitors, e.g. antithrombin III or α2-antiplasmin.

The concentration of the oxidant, e.g. chloramine-T®, in the oxidant reagent is usually 15–200 mmol/l, particulary 30–120 mmol/l, especially preferred 50–70 mmol/l. The oxidant is typically added in an amount of 15–200 μmol, particulary 30–120 μmol, especially preferred 50–70 μmol per ml sample fluid, particularly plasma. The oxidant can be present in physiol. NaCl and/or a buffer if appropriate, especially PBS (pH 7.4), NaHCO$_3$ (pH 8–9), or citrate (pH 7–9, preferred 7.4–8.4), preferably preferred sodium citrate in a concentration of 10–200 mM, particularly 20–100 mM, especially preferred 50 mM, if the relation sample oxidant reagent is 1:1.

Lower doses usually do not eliminate the disturbing influence of the plasma matrix on the *Limulus*-system; higher doses usually result in an increasing inactivation of LPS and/or lipid-A and/or glucans in plasma.

Additionally it has to be considered when performing the according to the invention procedure, that after performing the oxidation reaction there do not remain too large amounts of oxidant in the sample: the *Limulus*-factors C,B, A are only up to an addition of about 5 μmole chloramine-T® per ml plasma-sample resistant (in contrast to typical mammalian serine proteases, as e.g. trypsin or plasmin, that are at least 10 fold more resistant, why according to EP-A-297,597 no antioxidant is added). Therefore after performing the oxidation the remaining amount of oxidant should be inactivated if appropriate, e.g. by a quencher of singlet-oxygen. So when using e.g. 60 mM chloramine-T® the remaining amount of oxidant after the oxidaton time is neutralized by a singlet-oxygen quencher, e.g. ascorbate or preferably methionine, before the *Limulus*-factors are added to the reaction or singlet-oxygen-quencher and *Limulus*-factors are added at the same time.

Preferred amounts of oxidant, particularly chloramine, according to step a) in the sample are in the range between 20 to 100 μmol per ml plasma-sample.

The according to step b) used *Limulus* amebocyte— factors can be known reagents, that are produced by lysis of *Limulus*-amebocytes (so-called LAL), however they could also be produced gen-technically. Preferably used is here the Pyrochrome®-reagent, that compared to Coamatic® is more sensitive for LPS. References on LAL within this description have to be understand in such a way that also otherwise produced *Limulus* amebocyte—factors can be used.

In step b) single or all *Limulus* amebocyte—factors can be used. Preferred is the usage of a combination of the factors A, B and C.

The activation of at least one of the *Limulus* amebozyte (LA)-factors can be determined in a known manner, e.g. by measuring the gelation time, by measuring the amount of coagulin generated by LA-factors or preferably by measuring the by LA-factors released chromophore out of a chromogenic compound that is cleavable by activated LA-factors.

The samples to be used according to the invention can be arbitrary biologic liquids that may contain lipopolysaccharide and/or lipid-A and/or glucans. Examples herefore are blood, blood products, liquor, urine, saliva, bronchoalveolar lavage, ascites, pericardial or pleural effusions, milk, tissue liquids, lymph liquid and particularly plasma. Further samples to be used are products, preferred industrially manufactured products, that contain anti-*Limulus* factors, e.g. plasma protein therapeutics such as albumin or antithrombin III.

Furthermore it was found that heparin-containing biologic liquids can influence the test results despite oxidative treatment: e.g. even by oxidation with 1 part of 60 mM chloramine-T® per 1 part of plasma there is only then matrix-independence if the sample contains less than 1 IU/ml heparin.

Since patient plasma normally even under therapeutic heparinization contains less than 0.5 IU/ml heparin, nearly all patient plasmas can be analyzed for reactive LPS and/or lipid-A and/or glucan.

Samples with more than 1 IU/ml heparin, as they occur e.g. in patients under hemodialysis or extrapulmonary cardiac surgery with up to about 10 IU/ml heparin, should be oxidized with high doses of oxidant, e.g. with 100 μmoles chloramine-T® per ml plasma-sample, to obtain complete matrix-independence or the heparin should be neutralized by addition of a heparin inhibitor such as Polybrene®.

Preferably one works with comparably low concentrations of oxidants, to imitate better the pathophysiologic interaction between LPS or lipid-A or glucan, respectively, and sensible human cells (=LPS-reactivity or lipid-A-reactivity or glucan-reactivity, respectively): a concentration of about 60 mmol/l Chloramin-T® is more physiologic than one of 120 mmol/l in the oxidant reagent (chloramine-concentrations of about 10 mmol/l can be found in the microenvironment of activated neutrophil granulocytes). Due to this reason preferably concentrations of less than or equal to 100 mmol/l, particularly less than or equal to 60 mmol/l, oxidant, preferably chloramine-T, in the oxidant reagent (if 1:1 relation plasma sample:oxidant) are used, preferably in samples with less than 1 IU/ml heparin.

If appropriate a heparin inhibitor, e.g. Polybrene® (hexadimethrine bromide (1,5-dimethyl-1,5-diazaundecamethylene polymethobromide), Sigma, Deisenhofen, Germany product nr. H 9268) can be added to the sample. However, Polybrene® stimulates the LPS/*Limulus*-system, which is not in the sense of an imitation of the LPS/monocytes reactivity. Nevertheless according to the state of the art preferably heparin samples of the patient (of typically about 30–60 IU/ml heparin in plasma, e.g. Endo Tube ET, Chromogenix, Molndal, Sweden) are used for the *Limulus*-test.

Samples to be used according to the present invention contain less than 1 IU/ml heparin, and contain a calcium—complexing agent such as citrate or EDTA, whereby as calcium—complexing agent citrate is preferred. If appropriate a glucan-inhibitor and/or glucan-inactivator (as e.g. Zwittergent®, particularly Zwittergent® 3–14 (3-(N,N-dimethylmyristylammonio)propane sulfonate) and/or beta-1,3-D-glucanase (*Helix pomatia* or *Rhizoctonia solani*) can be added to the assay to increase the specificity for LPS or lipid-A.

The analysis of the claimed detection method may be effected with common methods, e.g. the Hyperbolic-Rate-Kinetic. A further purpose of the present invention is a procedure that converts the complicate Hyperbolic-Rate-Kinetic of the *Limulus*-test into a linear kinetic, facilitating enormously the evaluation.

It was found that by addition of at least one guanidine-compound, such as arginine or guanidine carbonate, and/or a chaotropic agent, e.g. an alkalimetal-cation, such as $K^+$, $Na^+$ or $Cs^+$ or one earthalkalimetal-cation, such as $Ca^{++}$ or $Mg^{++}$ before or during performance of step c) or together with the *Limulus*-factors a linear kinetic of the test is obtained.

Especially the elimination of the matrix-interference but also the linearization of the *Limulus*-test and the differentiation between reactivity of LPS or lipid-A on the one hand and glucans on the other hand allow for the first time routine suited determinations of LPS and/or lipid-A and/or glucan, particularly of free LPS and/or lipid-A and/or glucans, in body liquids of patients, as in their blood or in blood products.

Therefore, in a further arrangement of the procedure according to the invention the reactivity of LPS or Lipid-A can be differentiated from the reactivity of glucans, so that the reactivity of both groups of toxins can be determined. For this purpose the procedure described above is performed in presence and in absence of a LPS-inhibitor or lipid-A-inhibitor, respectively. The determined reactivities are substracted from each other and so the reactivity specifically caused by LPS and/or lipid-A is determined.

As LPS-inhibitor or lipid-A-inhibitor, respectively, e.g. Polymyxin-B (1 mg=7868 IU, Aerosporin, Euro OTC Pharma, Kamen, Germany; or from Sigma-Fluka, Deisenhofen, Germany) can be used.

To determine LPS- and/or lipid-A- and/or glucan-reactivity of the sample, the sample is first preoxidized by an oxidant, as a chloramine, and the reaction is preferably stopped by addition of an antioxidant. Following this or at the same time with the addition of the antioxidant the *Limulus*-test is performed in known manner and the samples are measured both in absence (approach A) and in presence of an endotoxin-inhibitor (approach B). From approach A the LPS+lipid-A+glucan reactivity of the sample can be determined, whereas approach B only reflects the glucan-reactivity. The difference of the measured reactivities, e.g. determined as the difference of the absorptions A–B of the released chromophores, results in the content of LPS- and lipid-A-reactivity in glucan-containing or glucan-free samples.

The measured and for PMB-own activity-corrected absorptions for approach B (Bcorr) can be converted in reactivities of glucans, e.g. in zymosan A like reactivity in μg/ml.

The difference of the absorptions A–Bcorr can be converted in reactivities of LPS and/or lipid-A, e.g. in LPS like reactivity in ng/ml.

The calibration curve of the test is under usage of the above described measures up to about 10000 ng/ml LPS in normal plasma, in particular between 200–300 ng/ml LPS, or up to about 100 μg/ml zymosan A in normal plasma, in particular between 2000–3000 ng/ml=2–3 μg/ml zymosan A, linear. These reactivities refer to pooled normal plasma that was supplemented with these amounts of LPS or lipid-A, respectively, or glucan.

Using the Hyperbolic-Rate-Assay-Kinetic plasmatic LPS-reactivities around 1 ng/ml (i.e. 0.1 to 5 ng/ml), are detectable after about 60–120 min at room temperature (RT, about 23° C.), around 10 ng/ml (i.e. 1 to 50 ng/ml) after about 30–60 min RT, around 100 ng/ml (i.e. 10 to 500 ng/ml) after about 15–30 min RT, around 1000 ng/ml (i.e. 100 to 5000 ng/ml) after about 8–15 min RT, around 10000 ng/ml (i.e. 1000 to 50000 ng/ml) after about 4–8 min RT, depending e.g. on the variability of the respective LAL-factors-production-charge.

Respective the plasmatic glucan-reactivities comparable values result, however the ng/ml multiplied by the factor 100.

If a sample contains higher values of reactive LPS and/or lipid-A and/or glucan, then the sample might be diluted with 3–10%, preferred 4–9%, especially 7% albumin, preferably human albumin, preferably in phosphate buffered saline (PBS) or with normal plasma.

The LPS- or lipid-A-, respectively, or glucan-reactivity does not show a "High-Dose-Inhibitory"-effect, i.e. extreme concentrations of LPS or lipid-A on the one hand or of glucan on the other hand, e.g. about 10000 ng/ml or 100 μg/ml, respectively, do not result in an inhibition of the *Limulus*-reaction.

The sample in the here described *Limulus*-test should have preferably a protein concentration that corresponds approximately to that of human plasma, i.e. 30–100 g/l, particularly 60–90 g/l.

Preferred the method in accordance with the invention, in particular the oxidation reaction and also the *Limulus* reaction, are carried out at temperatures between 0° C. and 50° C., in particular preferred between 15° C. and 45° C. Further the method will be carried out preferred under physiological conditions, in particular at a pH-value between 6 and 10, preferred between 7,0 und 9,5, especially preferred between 7,5 and 9,0. If necessary an appropriate buffer may be added to the biological fluid or the used reagents.

The invention concerns also a test system that is suited for the determination of lipopolysaccharide- and/or lipid-A- and/or glucan-reactivity. This comprises at least one oxidant and *Limulus* amebocyte-factors to treat the sample.

Especially preferred is a suited test system with linear kinetic to determine lipopolysaccharide- and/or lipid-A- and/or glucan-reactivity that contains additionally to the above mentioned reagents at least one linearization-reagent.

According to the invention is furthermore a test system that in addition to the above mentioned reagents contains at least one LPS- and/or lipid-A-inhibitor to differentiate between lipopolysaccharide- and/or lipid-A-reactivity of the sample on the one hand and glucan-reactivity of the sample on the other hand. An especially suited LPS-inhibitor is polymyxin-B, preferred in a concentration of 0.2–5 mg/ml plasma sample, especially preferred 1–3 mg/ml (corresponding to 10–30 μg polymyxin-B per 10 μl plasma).

A further purpose of the invention is the usage of this test system to determine lipopolysaccharide- and/or lipid-A- and/or glucan-reactivity in biological liquids.

In the following a typical performance of the test according to the invention to determine basal LPS- and/or lipid-A and/or glucan-reactivity is described. The assay is preferably performed in two approaches; however, both approaches can also be performed separately.

Approach A (Results in Basal (LPS+Lipid-A+Glucans)-Reactivity)

1 part sample (e.g. 10 μl) was incubated with 1 part 15–200 mmol/l, preferred 30–120 mmol/l, particularly 50–70 mmol/l chloramine-T (CT) in PBS or by addition of 0,1–2 μmoles, preferred 0,3–1,2 μmoles, particularly 0,5–0,7 μmoles CT in 0,1–100 parts PBS for 10 min at 37° C. (or for 30 min at room temperature). Then 1–5 parts, preferred 1 part, 100–230 mmol/l methionine in $H_2O$ or 1–11,5 μmoles methionine in $H_2O$ were added. After 0–5 min room temperature 0.5–5, preferably 2–3, parts *Limulus*-reagent with or without chromogenic *Limulus*-substrate were added (e.g. Pyrochrome®, which had priorly been reconstituted with the by the manufacturer indicated amount of tris buffer, usually 3,2 ml 200 mmol/l tris, pH 8, for the *Limulus*-assay in Hyperbolic-Rate-Kinetic). If appropriate the antioxidant and/or the LPS-inhibitor can already be present in the reconstitution material for the *Limulus*-factors or in the lyophilisate of the *Limulus*-factors. To increase specificity of the chromogenic substrate for *Limulus*-factors the antioxidant-reagent might contain a trypsin-inhibitor, particularly aprotinin, preferably in a concentration of 100–10000 KIU/ml, particularly 200–2000 KIU/ml and/or aprotinin-doses of 100–10000 KIU, particularly 200–2000 KIU per ml sample might be added to the reaction.

The absorption was immediately determined (BASE-value) and after 1–10 min (at room temperature). Thereby an eventually present linear control absorbance increase (delta $A_c$) was determined. If the sample contained trypsin or a trypsin-like activity, as in pancreatitis (about 10–100 ng trypsin/ml) the here eventually determined linear delta $A_c$/min had to be subtracted from all in the Hyperbolic-Rate-Assay determined values.

Then either at room temperature the increase in absorbance (delta A) in 2–15 min distance was determined (Hyperbolic-Rate-Kinetic), or after 0,5–300 min, preferred 5–100 min, particularly 10–50 min, especially preferred 15–30 min (RT) and/or when in the 10 or 100 ng/ml LPS-reactivity-standard a delta A of 3–30%, particularly about 15% of the maximally obtainable delta A occurred, 1–20 parts, preferably 5–10 parts, especially 5 parts linearization reagent were added, consisting of a guanidine-compound as arginine and/or a chaotropic agent as alkali-cations as $K^+$, $Na^+$ or $Cs^+$ or earthalkali-cations as $Ca^{++}$ or $Mg^{++}$ (final concentration preferably 75–750 mmol/l; preferred concentration in the added reagent=100–1000 mmol/l, if appropriate with 0,1–2 mmol/l final concentration of chromogenic substrate) and the delta A/t was determined. Substrate was added preferably in the case if priorly no substrate was present in the *Limulus*-reagent.

The addition of the linearization reagent transformed the hyperbolic into a linear kinetic.

If appropriate up to 50 mmol/l, particularly up to 30 mmol/l, arginine (specificity reagent) was added already in the first LAL-incubation phase, because arginine increased the specificity, however it also decreased the reaction velocity.

Instead of arginine according to the invention also another gunidinium-group wearing substance can be chosen both for the linearization reagent and for the specificity reagent, as e.g. guanidine carbonate, the pH value of these reagents should be between 7 and 10, particularly between 7,5 and 9,5.

Approach B (Results in Basal Glucan-reactivity)

The incubation conditions were identical to approach A with the change that additionly polymyxin B was used: 0.01–100 mg/ml plasma sample, preferred 0.1–10 mg/ml plasma sample, particularly 0.2–5 mg/ml plasma sample, especially preferred 1–3 mg/ml polymyxin B (corresponding to 10–30 µg polymyxin B per 10 µl plasma; 1 mg=7868 U).

15000 U/ml polymyxin B neutralized up to 10000 ng/ml LPS-reactivity in pooled normal plasma in the here described *Limulus*-system.

The determined delta A value for pooled normal plasma (without zymosan A) was subtracted from all delta A values. This was a delta A, that was induced by the polymyxin B added, and that had to be subtracted from all B-values.

If after this correction the patient had positive delta A-values, then these were the reactivity caused by glucans.

If the sample had less than 50 ng/ml LPS reactivity, then approach B could be performed with 10-fold less addition of polymyxin-B, i.e. especially preferred 0,1–0,3 mg/ml plasma-sample. This resulted into a better sensitivity of the assay.

The in the B-approach determined and corrected values (PMB-Base-Line=Activity in normal plasma) have to be subtracted from those of the A-approach. So the LPS-reactivity in the investigation material was determined

[LPS+Lipid-$A$+Glucans]−[Glucans]=[LPS+Lipid-$A$].

Approach C (Results in Trypsin-like-activity)

as A, linearization reagent was added before (or if appropriate up to 3 min after) the *Limulus*-reagent; the further incubation after addition of the *Limulus*-reagent was not necessary.

Approach C results in the trypsin-like-activity (TLAC), in the normal case not present; positive e.g. in pancreatitis, intensive-care-unit-patients with coagulation activation, cooled plasma samples, or in nonfresh *Limulus*-reagent positive. The TLAC expressed in mA/min must be subtracted from all values determined in A und B.

As standards for the procedure according to the invention e.g. pooled normal plasma (or 7% human albumin) was analyzed with a basal LPS-reactivity (BL) of 0,2–2 ng/ml LPS, particularly of 0,4–1,2 ng/ml LPS, that was supplemented with 0, 1, 10, 100, 1000, 10000 ng/ml LPS. These calibration standards had by definition LPS-reactivities as 0+BL, 1+BL, 10+BL, 100+BL, 1000+BL, 10000+BL ng/ml LPS in normal plasma. Further calibration standards had 0, 0.1, 1, 10, 100 µg/ml zymosan A. If appropriate additionly with a trypsin-control (e.g. 100 ng/ml trypsin in 7% albumin-PBS) can be standarized, to determine the content of active trypsin in the sample.

As standards substrates were chosen, that had a matrix—i.e. a surrounding of the analyte—that was similar to the surrounding in which the analyte of the samples was enbedded. Suitable sample material are particularly citrate- or EDTA-plasmas. When analyzing EDTA-samples the standards should contain also EDTA.

If a sample with a matrix different from plasma is to be analyzed, e.g. liquor cerebrospinalis, urine bronchoalveolar lavage, milk, a blood product, a commercial factor concentrate or saliva (saliva contains physiologically 100–500 ng/ml LPS reactivity, which is one reason for the *Limulus*-assay being so trouble-prone) then the sample should be brought with pooled plasma or if appropriate with 7% human albumin by a dilution of 1+2 to 1+100, particularly of 1+4 to 1+9, before it is analyzed in the here described assay.

Alternatively, an addition calibration can be performed, i.e. addition of known amounts of LPS or lipid-A or glucan to a sample, e.g. a commercial antithrombin III drug, and determination of the LPS- or lipid-A- or glucan-reactivity in the supplemented and in the nonsupplemented sample. The absorption-difference is equivalent to the added LPS- or lipid-A- or glucan-amount and is a measure for the basal LPS-, lipid-A- or glucan-amount.

Normal plasma has about 0,8 ng/ml LPS-reactivity (mean valuet=MV; i.e. it reacts, if a plasma without LPS-reactivity was supplemented with 0,8 ng/ml LPS. 1 standard deviation (SD)=0,4 ng/ml LPS reactivity. The intra-assay variation coefficients are below 10%.

Septic patients have up to about 200 ng/ml, sometimes>200 ng/ml LPS-reactivity and/or up to 10 µg/ml, sometimes>10 µg/ml glucan-reactivity in plasma. The lower detection limit of the assay according to the invention is about 0.1 ng/ml LPS-reactivity and/or about 0.1 µg/ml glucan-reactivity in plasma.

Only about 1% of the LPS added to pooled normal plasma reacts in the procedure according to the invention as LPS reacts when added to 7% human albumin reagiert, i.e. plasma contains LPS-inhibitors, inhibited LPS is not detected in the present procedure. Only about 10% of the glucan added to pooled normal plasma reacted in the procedure according to the invention as glucan reacts when added to 7% human albumin, i.e. the present procedure does not detect neutralized glucans.

Plasma samples should be analyzed undiluted if possible, because so the pathophysiologic LPS- and/or lipid-A- and/or glucan-reactivity is best imitated.

The incubation times at room temperature (RT, about 23° C.) are shortened 3-fold, if it is incubated at 37° C. Since the Limulus-system is extremely heat-sensitive, the incubation temperature should not exceed 37° C. if possible.

Only delta A values less than 45% of the maximally reachable delta A are evaluated.

In the following list the best performance form for approach A is presented. Then the best performance forms for approaches B and C are described.

Determination of the LPS and/or Lipid-A and/or Glucan-reactivity (Approach A)

---

10 µl Sample
10 µl Oxidant-Reagent (60 mM CT)
10 µl Antioxidant-Reagent (230 mM methionine)
3 min RT
30 µl Limulus-Reagent (e.g. Pyrochrome ®, rekonst. in 3.2 ml Tris buffer)
Test without linearization of kinetic:
delta A/t
or
If appropriate, test with linearization of kinetic:
20 min RT or 40 min RT
50 µl Linearization-Reagent (750 mM arginine, pH 8.7)
delta A/t

---

Determination of the basal glucan-reactivity (Approach B)
As approach A, antioxidant-reagent contains additionally 15000 U/ml polymyxin B
Determination of trypsin-like-activity (Approach C)

Test without linearization: as approach A, determination of an eventually present linear delta A/t increase within the first 1–10 min RT of approach A and B.

Test with linearization: as approach A, linearization reagent is added prior to (or if appropriate up to 3 min after) the linearization reagent; the 20 min or 40 min RT incubation prior to addition of linearization reagent is omitted.

If it is incubated at 37° instead of RT, then the incubation times are shortened three-fold.

Additionally to the basal LPS- and/or lipid-A- and/or glucan-reactivity (approaches A, B) the LPS- and/or lipid-A- and/or glucan-reactivity could be tested, after additionly LPS or lipid-A or glucans had been added to the sample. So the individual inhibition capacity against LPS and/or lipid-A and/or glucans was tested.

Patients with low LPS/lipid-A/glucan-inhibition capacity (e.g. few respective antibodies or LBP in plasma) are more susceptible for pathologic DIC. This was tested in the next described approaches D or E.

Approach D (Results in Added LPS-and/or Lipid-A-reactivity=LPS-and/or Lipid-A-inhibition Capacity)

Approach A was performed with the change that to the sample 0.5 parts 1–1000, preferred 2–50, particularly 10 ng/ml LPS were added and if appropriate prior to the oxidation it was incubated for 1–60 min RT: 100% of norm=increase by 5 ng/ml LPS-reactivity; SD=50%, patients have up to about 1000–10000% of norm.

Approach E (Results in Added Glucan-reactivity=Glucan-inhibition Capacity)

Approach A was performed with the change that to the sample 0.5 parts of 0.1–100, preferred 0.4–4, especially preferred 1 µg/ml zymosan A were added: 100% of norm=increase by 0.5 µg/ml glucan-reactivity; SD=20%, patients have up to about 100–1000% of norm.

Die following examples describe the procedure according to the invention without limiting it.

In the FIGS. 1 to 24 are presented the measuring results of the procedure according to the invention.

EXAMPLE 1

Approach A

10 µl plasma of the patient and plasma-standards with 0,1,10, 100, 1000, 10000 ng/ml LPS-reactivity were incubated in duplicate with 10 µl 60 mM chloramine-T® in PBS for 10 min at 37° C. (or 30 min at room temperature=RT). Then 10 µl 230 mM methionine in H$_2$O was added. After 3 min RT 30 µl Limulus-reagent with chromogenic Limulus-substrate S-2834® was added (Pyrochrome®). The absorption was determined after 2 min (RT; BASE-value) and after 4 min (RT; trypsin-control for Hyperbolic-Rate-Kinetic). After 20 min (RT) the linearization-reagent was added, here 50 µl 750 mM arginine, pH 8,7 (final concentration 341 mM) and the delta A/t was determined.

This value corresponded to the (LPS+lipid-A+glucan)-reactivity of the sample.

EXAMPLE 2

Approach B

Incubation conditions identical to approach A, changing the measured standards: 0, 1, 2, 4, 8, 16, 32 µg/ml zymosan A in pooled glucan-free normal plasma. The methionine-reagent contained additionally 15000 U/ml polymyxin B (PMB). The delta A value determined for pooled normal plasma (without zymosan A) was substracted from all in approach B determined delta A values (PMB-correction). The PMB-corrected B-value corresponded to the glucan-reactivity of the respective sample. The in the B-approach determined and PMB-corrected values had to be subtracted from those of the A-approach: so one got the LPS+lipid-A-reactivity of the sample [LPS+lipid-A+glucans]−[glucans]= LPS+lipid-A.

EXAMPLE 3

Approach C

Incubation conditions identical to approach A, changing that the linearization reagent was added prior to the Limulus-reagent and the increase in absorption (delta A) was determined directly.

EXAMPLE 4

Approach D

Identical incubation conditions as in approach A, changing that 5 µl 10 ng/ml LPS was added to the sample and it was incubated for 10 min RT prior to the oxidation.

EXAMPLE 5

Approach E

Identical incubation condition as in approach A, changing that 5 µl 1 µg/ml zymosan A was added to the sample and it was incubated for 10 min RT prior to the oxidation.

EXAMPLE 6

Hyperbolic Rate-Kinetic with Pyrochrome®-reagent 1 ml pooled patient plasma (citrate; containing 1,8 ng/ml LPS reactivity) with normal plasmatic coagulation was supplemented with 0–10000 ng/ml LPS (Sigma, *E. coli* B5, gel-filtered) or with 1 µg/ml zymosan A (Sigma) and incubated with 1 ml 60 mM chloramine-T® (=CT) in PBS for 10 min (37° C.) in pyrogen-free U-microtiterplates. 1 ml 230 mmol/l methionine in $H_2O$ was added (comparable to 3,33 µl sample+3,33 µl 60 mM CT+3,33 µl 230 mM methionine) and after 3 min (room temperature) 10 µl of this mixture was incubated with 5 µl $H_2O$ or 10000 U/ml polymyxin B (Euro OTC Pharma, Kamen, Germany) in $H_2O$ und 5 µl $H_2O$ (approach 1a) or 240 mM arginine (approach 1 b), pH 8.7 (30 mmol/l final) and 20 µl Pyrochrome®-Reagent at room temperature.

The absorption-values of the experiment performed according to example 6 were determined after 0–44 min (RT) at 405 nm bestimmt. The values represented in FIGS. 1–3 were determined.

FIG. 1 demonstrates, that usage of 20 µl *Limulus*-reagent (with chromogenic substrate-colyophilisate; sample amount=3,3 µl) results into a maximal delta A of 470 mA; a delta A of 100 mA (corresponding to about 20% of the max. delta A) results for 1,7 ng/ml LPS-reactivity in plasma after 37 min RT, for 3,2 ng/ml LPS-reactivity after 32 min RT, for 6,3 ng/ml LPS-reactivity after 26 min RT, for 15,4 ng/ml LPS-reactivity after 24 min RT, for 42,9 ng/ml LPS-reactivity after 23 min RT, for 125 ng/ml LPS-reactivity after 22 min RT, for 373 ng/ml LPS-reactivity after 18 min RT.

Figure 2:
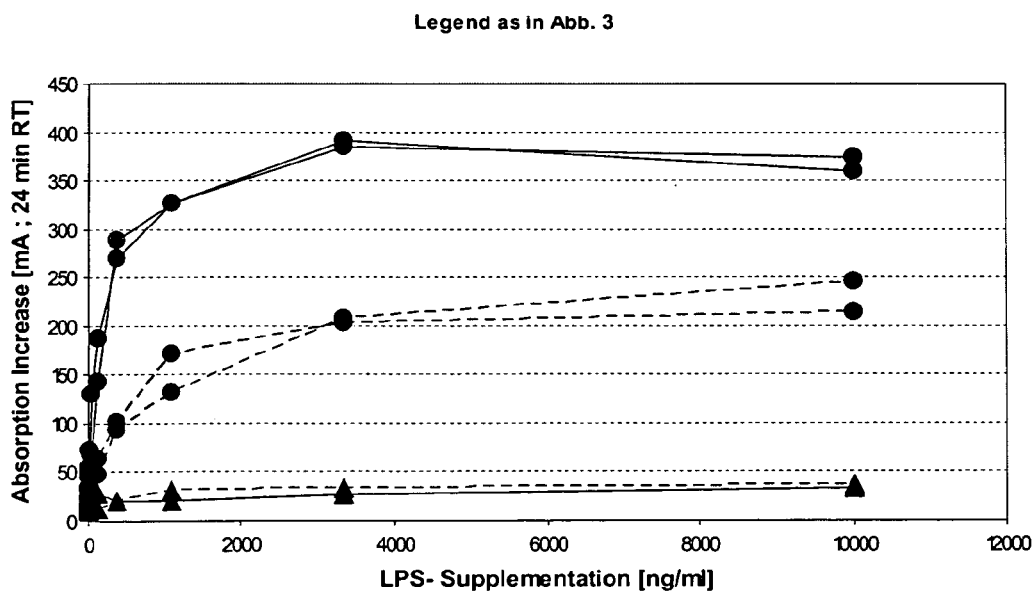

FIG. 2 shows, that usage of 3,3 µl sample, 3,3 µl oxidant, 3,3 µl methionine, 10 µl $H_2O$ or arginine and 20 µl Pyrochrome®-reagent and 24 min RT incubation result into a linearity of the *Limulus*-assay up to about 100–300 ng/ml LPS-supplementation to normal plasma, corresponding to 300 ng/ml LPS-reactivity. Without addition of 30 mM final arginine as specificity reagent the extinction for 10000 ng/ml LPS-reactivity is only by about 5% lower compared to that for 3333 ng/ml LPS-reactivity (•-• in duplicate determination), i.e. the assay does not have a high-dose-inhibitory-effect.

If 30 mM arginine is used as specificity reagent (•- -• in duplicate determination), then the *Limulus*-reaction is slowed down, a delta A of 200 mA after 24 min RT is reached without 30 mM arginine by supplementation of plasma with about 100 ng/ml LPS, with 30 mM arginine by supplementation of plasma with about 3000 ng/ml LPS. Addition of 50 µl 10000 U/ml PMB inhibits every LPS-supplementation up to 10000 ng/ml (▲).

Figure 3:
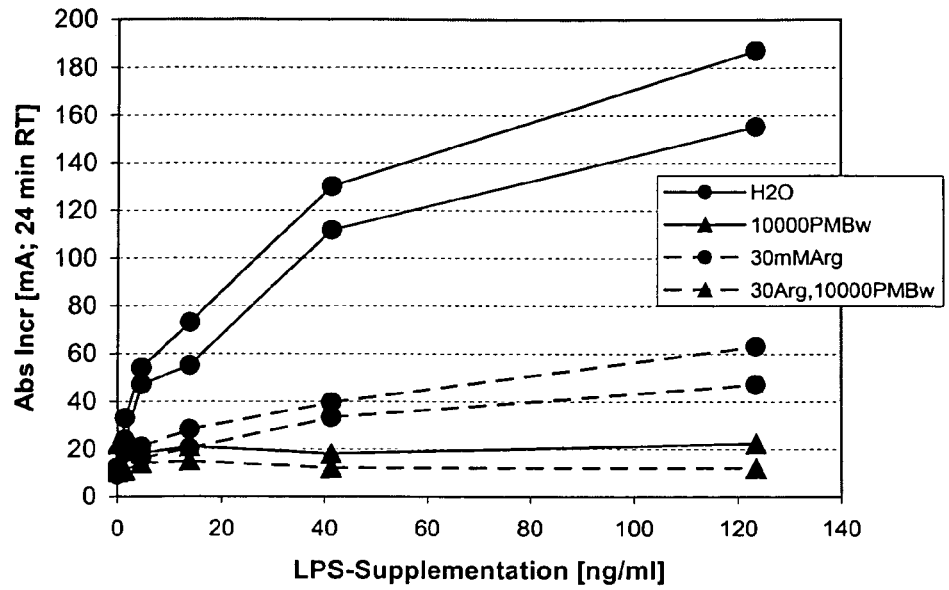

FIG. 3 demonstrates the Hyperbolic-Rate-Assay in this experiment in the lower range of LPS-supplementation.

Figure 4:
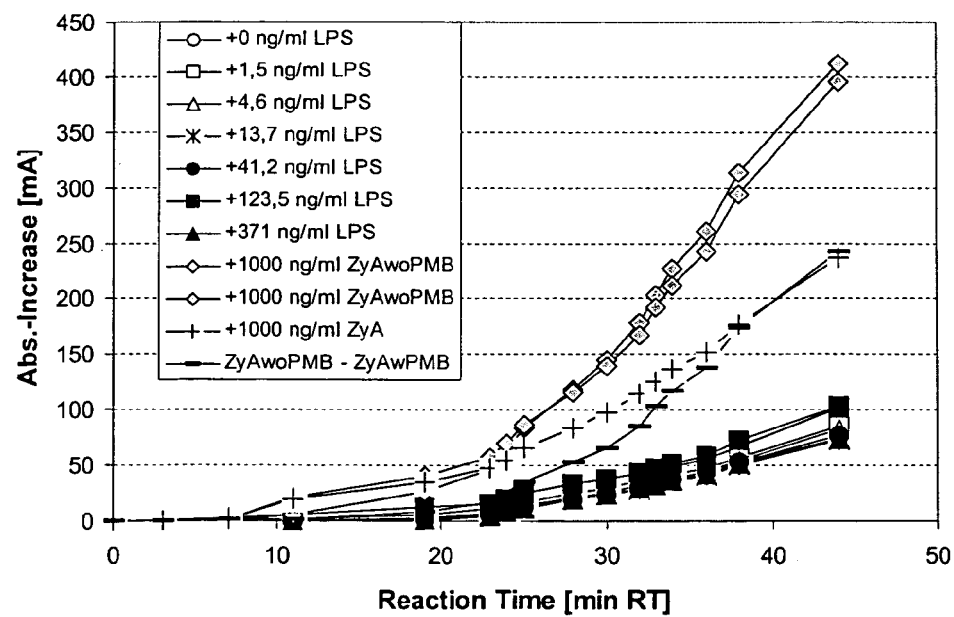

In FIG. 4 the inhibition of LPS by polymyxin B and the basal activity of polymyxin B itself on the *Limulus*-system is represented. Consequently, all with polymyxin B obtained delta A values had to be corrected by subtraction of the basal polymyxin B-delta A value for glucan-free plasma. If the so corrected polymyxin-B value is subtracted from that of approach A (see FIG. 1), then the LPS- and/or lipid-A-reactivity of the patient is obtained.

FIG. 4 demonstrates, that 5 µl 10000 U/ml PMB addition result into a delta A of about 70 mA after 44 min RT even in glucan-free pooled plasma (○). The figure shows, that LPS-supplementation of up to 371 ng/ml to normal plasma is completely neutralized by PMB in the first 44 min RT *Limulus*-reactions-time. 1000 ng/ml zymosan A with PMB (+) or without PMB (♦) can be detected without interference; (−) shows the difference of 1000 ng/ml zymosan A (ZyA) with PMB minus the PMB-itself control (○).

Figure 5:
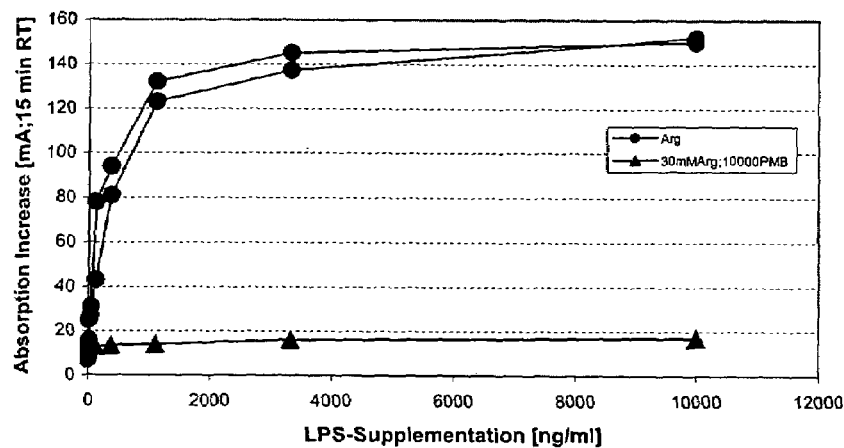

In FIG. 5 it is shown, how a linear Rate-Kinetic can be generated in the performance of the procedure according to the invention. So e.g. the kinetic of approach 1 b was linearized by addition of 50 µl 750 mM arginine, pH 8,7 (final arginine-concentration 30+417=447 mmol/l) 23 min at RT after addition of the LAL-reagent.

The 30 mM final arginine-approach represented in FIG. 5 was linearized with 50 µl 750 mM arginine (•). Linear extinction increases result, here as increase/15 min RT represented. A test linearity of up to about 300 ng/ml LPS-reactivity result. Even 10000 ng/ml LPS-reactivity does not result into a High-Dose-Inhibitory-Effect. 5 µl 10000 U/ml PMB-addition neutralizes the LPS-reactivity up to 10000 ng/ml (▲), if the linearization time point is 23 min RT.

Figure 6:
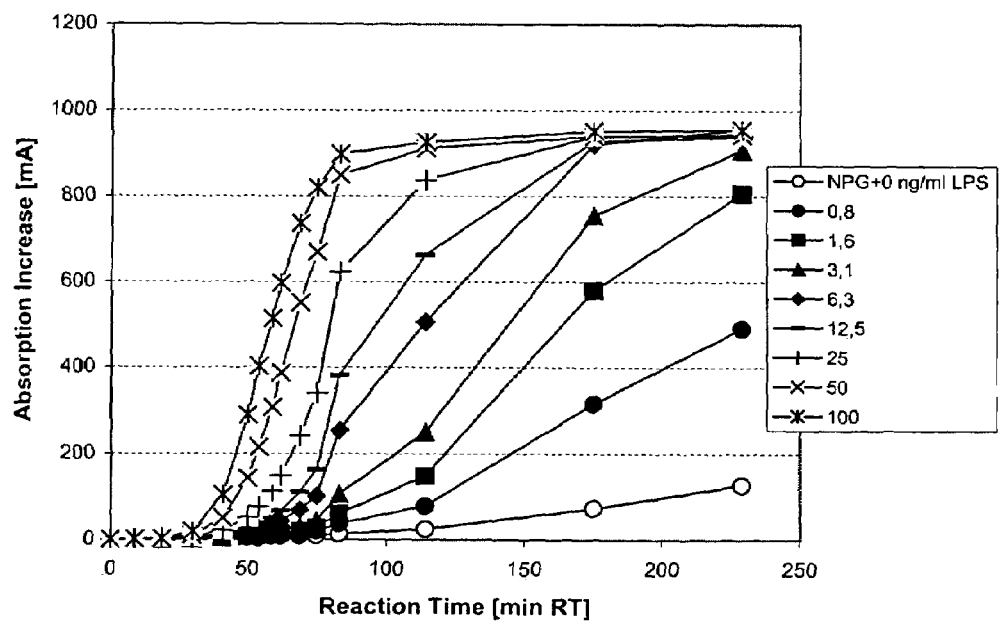
Figure 7:
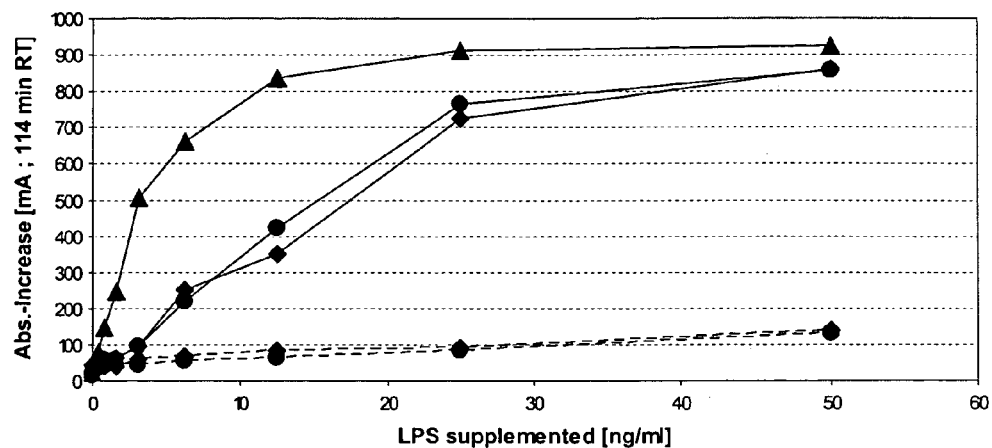

In the FIGS. 6 and 7 the performance of the procedure according to the invention is presented, using a Hyperbolic-Rate Assay with Coamatic®-Reagent in comparison to a Hyperbolic-Rate Assay with Pyrochrome®-Reagent.

Figure 8:
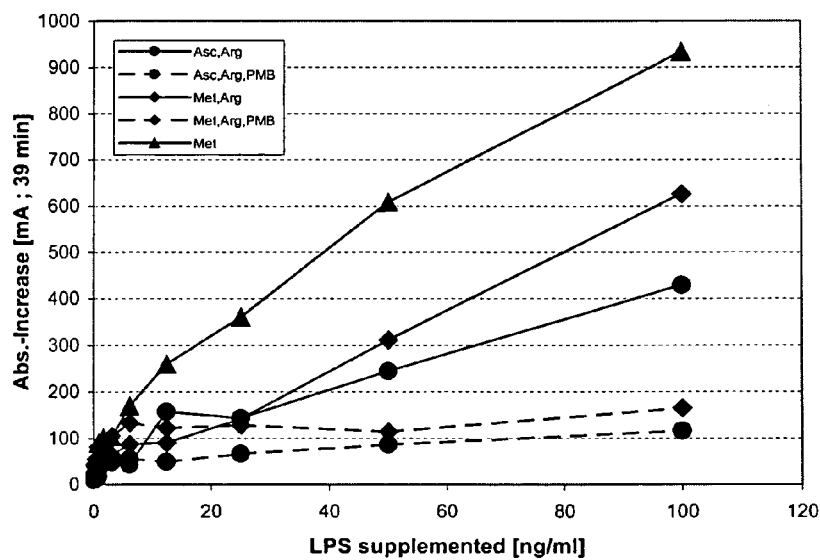

Therefore 10 µl pooled normal plasma, supplemented with 0–100 ng/ml LPS, was incubated with 10 µl 60 mmol/l CT for 10 min at 37° C. 10 µl 200 mmol/l methionine with 2000 U/ml polymyxin B (Sigma) were added and after 3 min RT 30 µl LAL-reagent Coamatic® (Chromogenix, Mölndal, Sweden) were added and at 23° C. or 37° C. incubated. FIGS. 7 and 8 demonstrate, that the Coamatic®-Reagent has a substantially slower kinetic than the Pyrochrome®-reagent, i.e. Coamatic-reagent contains less factor C but more chromogenic substrate than Pyrochrome®.

FIG. 6 shows, that 20% of the max. delta A are about 200 mA; this delta A is reached after 40 min RT for +100 ng/ml LPS, after 50 min RT for +50 ng/ml LPS, after 60 min RT for +25 ng/ml LPS, after 70 min RT for 12,5 ng/ml LPS, after 75 min RT for +6,3 ng/ml LPS, after 100 min RT for +3,1 ng/ml LPS, after 120 min RT for +1,6 ng/ml LPS, after 140 min RT for +0,8 ng/ml LPS, after about 270 min RT for +0 ng/ml LPS. The Coamatic®-Reagent is substantially more insensitive for LPS than the Pyrochrome®-reagent.

FIG. 7 shows, that 2000 U/ml PMB inhibit completely only up to about 20 ng/ml LPS-reactivity, that 50 ng/ml LPS inspite of 2000 U/ml PMB result into a delta A of additional 100 mA, that corresponds to a LPS-reactivity of +1 ng/ml. 30 mM arginine inhibits the LAL-system of Coamatic® substantially less than that of Pyrochrome®.

In FIG. 8 the influence of the addition of ascorbate and methionine in the procedure according to the invention is presented. Therefore pooled normal plasma was supplemented with 0–100 ng/ml LPS. 10 µl of it were incubated with 10 µl 60 mmol/l CT for 10 min at 37° C. 10 µl 210 mmol/l ascorbate or 210 mmol/l methionine with or without 210 mmol/l arginine in each case with or without 2000 U/ml polymyxin B were added. After 3 min at RT 30 µl LAL-reagent Coamatic® was added and at 37° C. incubated. The increase in absorption was determined. One sees that both ascorbate and methionine are suitable to neutralize the oxidation.

From FIG. 8 it can be seen, that the value for +0 ng/ml LPS can only be assessed correctly if the incubation time is prolonged to more than 100 min RT. The prolonged incubation time allow a better determination of the LPS-reactivities below 5 ng/ml LPS.

Figure 9:
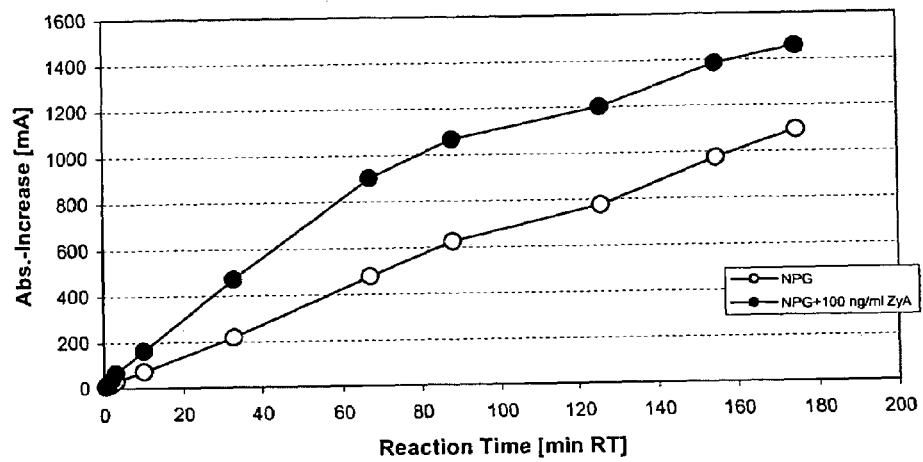

In FIG. 9 a procedure according to the invention is presented, in which the reactivity of 100 ng/ml zymosan A in pooled normal plasma was determined. Therefore 10 μl pooled normal plasma was supplemented with 0 or 100 ng/ml zymosan A and with 10 μl 60 mmol/l CT for 10 min at 37° C. incubated. Then 10 μl 200 mmol/l methinine with 2000 U/ml polymyxin B were added. After 3 min (RT) 30 μl LAL-reagent Coatest® (Limulus-factors not as colyophilisate with a chromogenic substrate) was added. After 40 min at 37° C. 75 μl 750 mM arginine, pH 8,7 and 25 μl 2 mmol/l CS-2834® were added and the increase in aborption at RT was measured gemessen. FIG. 9 demonstrates, that 100 ng/ml zymosan can be measured clearly.

FIG. 9 shows, that the maximal deflection is about 1800 mA, obtained by 25 μl 2 mM S-2834®, corresponding to 30 μl 1,7 mM chromogenic substrate (CS), i.e. in the Coamatic®-reagent are about 0,55 mM CS and in the Pyrochrome®-Reagent about 0,33 mM CS as a colyophilisate.

Figure 10:
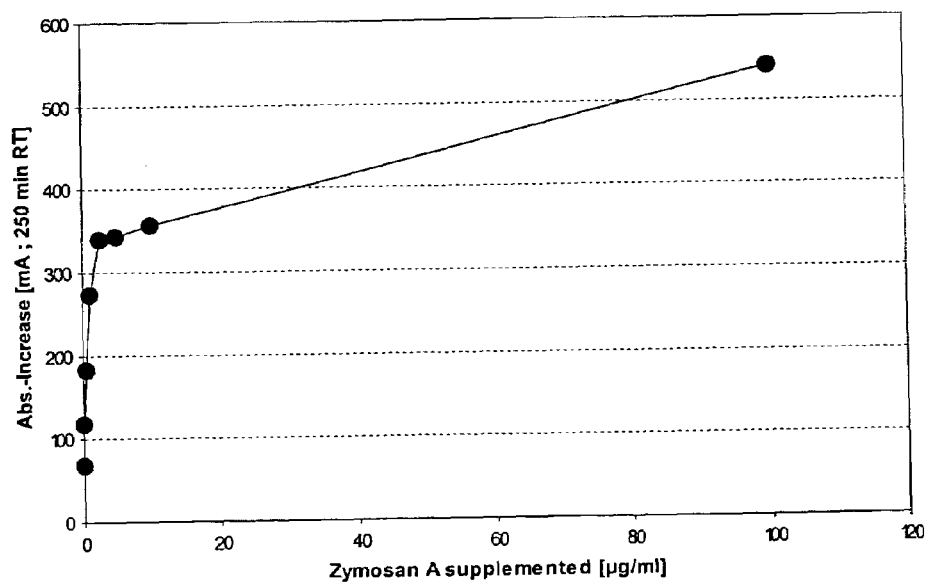

FIG. 10 shows the results of a procedure according to the invention, in which 10 μl pooled normal plasma, supplemented with 0–100 μg/ml zymosan A was incubated with 10 μl 60 mmol/l CT, 30 mmol/l NaHCO$_3$ for 30 min at RT. Then 10 μl 215 mmol/l methionine, 150 mmol/l arginine, pH 8,7, and 1000 U/ml polymyxin B was added and after 3 min (RT) 15 μl LAL-reagent Coamatic® was added and delta A determined. The test here is linear up to 2 μg/ml zymosan A.

Figure 11:
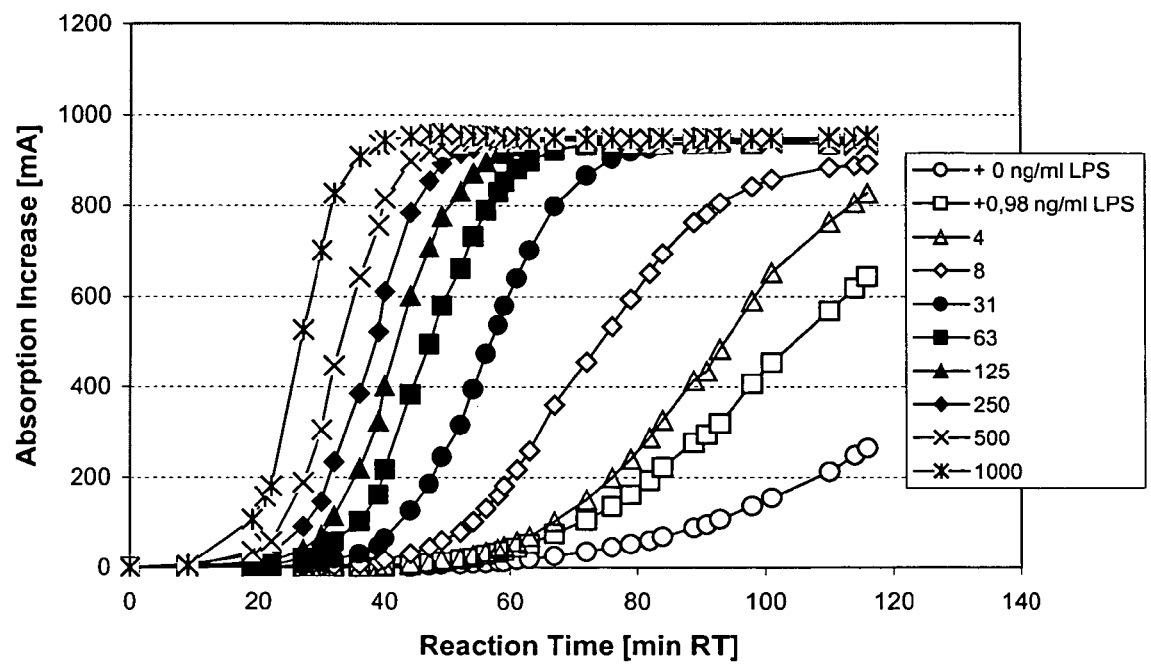

FIG. 11 shows the results of a procedure according to the invention, in which 10 μl normal plasma (Citrol; DadeBehring, Marburg, Germany) supplemented with 0–1000 ng/ml LPS was incubated with 10 μl 60 mmol/l CT. After 30 min at RT 10 μl 210 mmol/l arginine, 210 mmol/l sodium ascorbate and 30 μl LAL-reagent Coamatic® was added and delta A at 405 nm measured. FIG. 11 shows the kinetic at room temperature.

From FIG. 11 it can be seen, that a delta A of 200 mA, i.e. about 20% of the max. delta A, is reached for +1000 ng/ml LPS after 20 min RT, for +500 ng/ml LPS after 25 min RT, for +250 ng/ml LPS after +30 min RT, for +125 ng/ml LPS after 32 min RT, for +63 ng/ml LPS after 37 min RT, for +31 ng/ml LPS after 45 min RT, for +8 ng/ml LPS after 57 min RT, for +4 ng/ml LPS after 72 min RT, for +1 ng/ml LPS after 80 min RT, for +0 ng/ml LPS after 108 min RT. Thus, the LPS-kinetic for Coamatic® is substantially slower than that for Pyrochrome® (FIG. 1), particulary for samples supplemented with low amounts of LPS (here by the factor 2–3).

Figure 12:
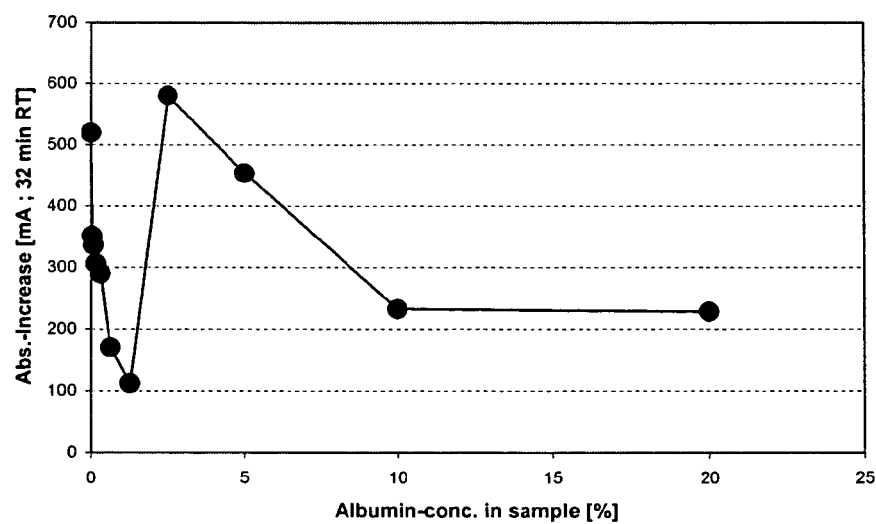

FIG. 12 shows the results of a procedure according to the invention, in which 10 μl 0–20% human albumin supplemented with 5 ng/ml LPS was incubated with 10 μl 60 mmol/l CT for 10 min at 37° C. Then 10 μl 200 mmol/l methionine and 30 μl LAL-reagent Coamatic® was added and delta A at RT was measured. One recognizes the strong dependence of the Limulus-test on the protein content of the sample.

FIG. 12 demonstrates, that an increase of the albumin-concentration of the sample from 0% to 1% results into a decrease of the LPS-reactivity to about ⅓ of the initial value. If the albumin-concentration is elevated to about 2%, then the initial value results again. If the albumin concentration of the sample continues to increase from 2% to 10%, then the LPS-reactivity falls to ⅓ of the initial value; a further increase of the albumin concentration of the sample from 10% to 20% does not result into a change of the LPS-reactivity of the sample. Thus, albumin stabilizes LPS (e.g. against binding to the plastic wall of the plate), but at the same time it inhibits the LPS-reactivity with Limulus-factors.

Figure 13:
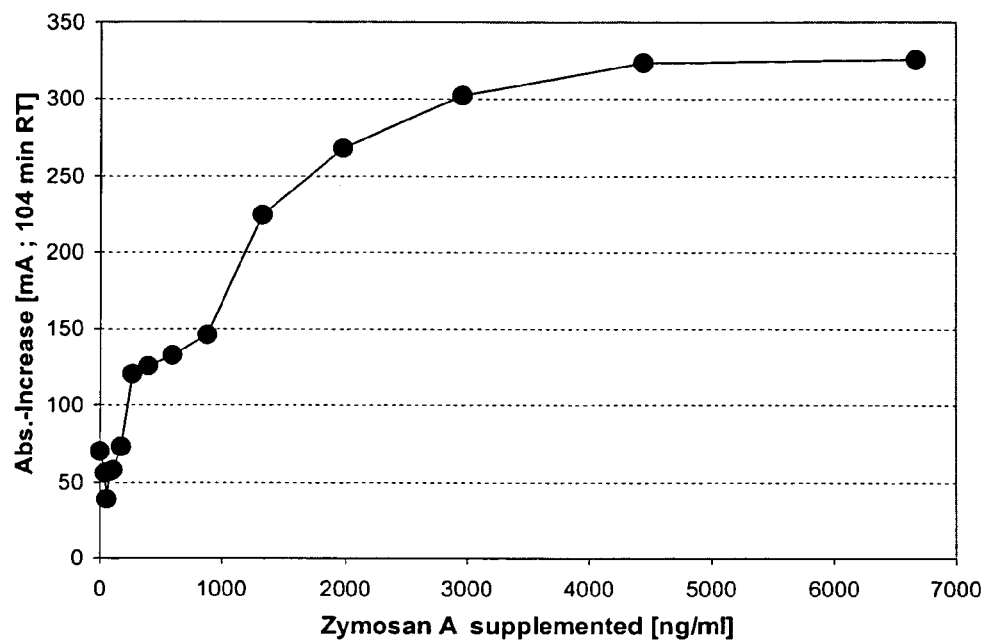

FIG. 13 shows the results of a procedure according to the invention, in which 10 μl pooled normal plasma (NPG) supplemented with 0–6667 ng/ml zymosan A was incubated with 10 μl 60 mmol/l CT for 10 min at 37° C. Then 10 μl 200 mmol/l methionine and 30 μl LAL-reagent Coamatic® was added and delta A at RT was measured. One recognizes the linearity (relation of glucan-concentration to resulting delta A) of the Limulus-test for glucans here up to a plasma concentration of about 2 μg/ml glucans.

Figure 14:
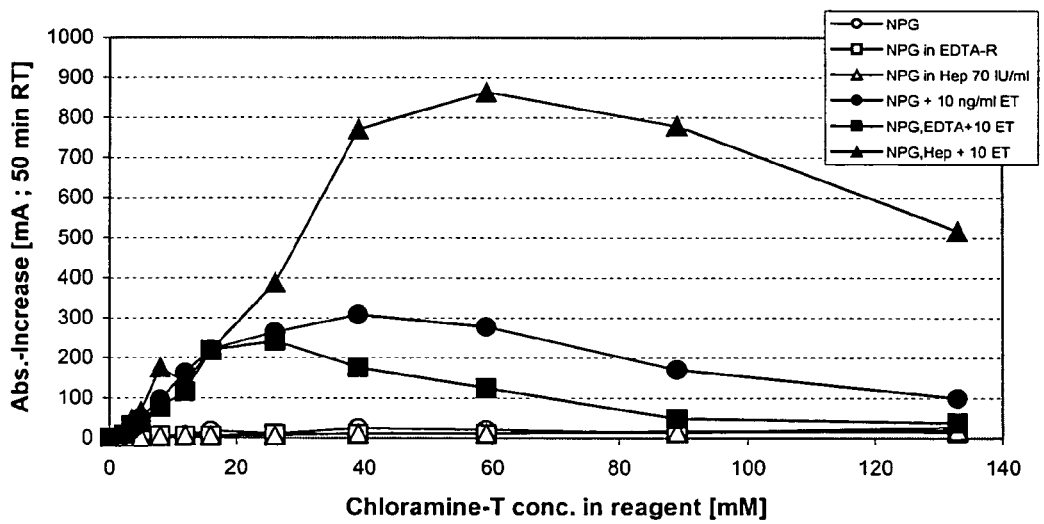
Figure 15:
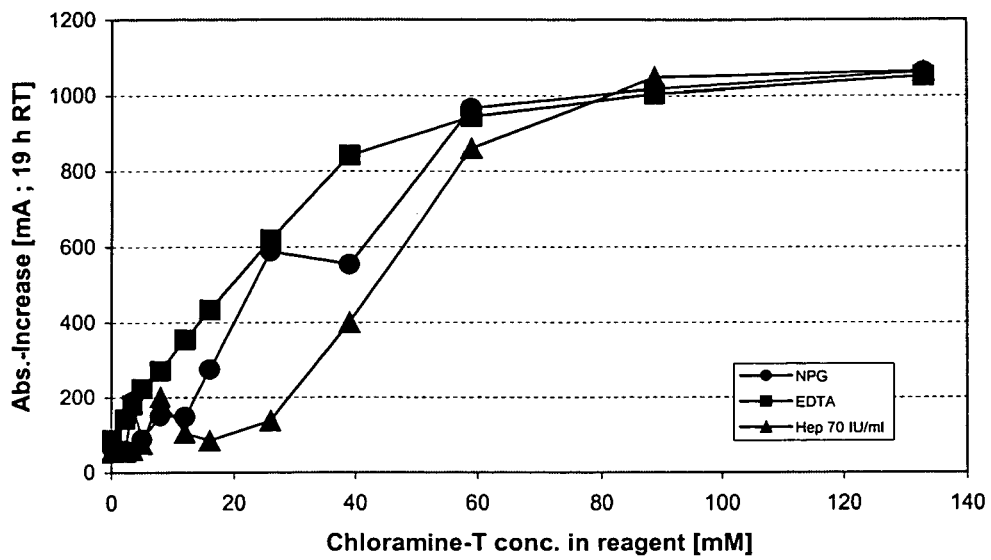

FIGS. 14 and 15 show the results of a procedure according to the invention, in which 10 μl sample (NPG, NPG plus 3,2 mg/ml EDTA, NPG plus 70 IU/ml heparin) supplemented with 0 or 10 ng/ml LPS was incubated with 10 μl 0–133 mmol/l CT in H$_2$O for 10 min at 37° C. Then 10 μl 200 mmol/l ascorbate and 30 μl LAL-reagent Coamatic® were added. FIG. 14 (for 10 ng/ml supplemented plasmas) and FIG. 15 (for unsupplemented plasmas) show, that CT—concentrations of 40–80 mmol/l are optimal to eliminate the heparin effect.

FIG. 14 shows, that without oxidation there appears no measurable LPS-reactivity within 50 min RT. 70 IU/ml heparin in the sample stimulate the LPS-reactivity about 5-fold when using an oxidant reagent with ≧60 mM CT. Since the procedure according to the invention shall imitate the pathophysiologic reactivity of LPS and/or lipid-A and/or glucans with human receptors for LPS and/or lipid-A and/or glucans (e.g. CD 14 or phospholipases of monocytes), instead of heparin-tubes—as according to the state of the art—according to the invention preferably citrate- or EDTA-monovettes are recommended for sampling.

FIG. 15 shows, that without oxidation there appears only a Limulus-reactivity of <100 mA/19 h RT for normal plasma. Addition of 40–80 mM CT increases the reactivity more than 10-fold. At least 60 mM CT in the oxidant reagent are necessary to result into a similar LPS-reactivity in heparinized plasmas (70 IU/ml in sample) as compared to pooled normal citrate- or EDTA plasma.

Figure 16:
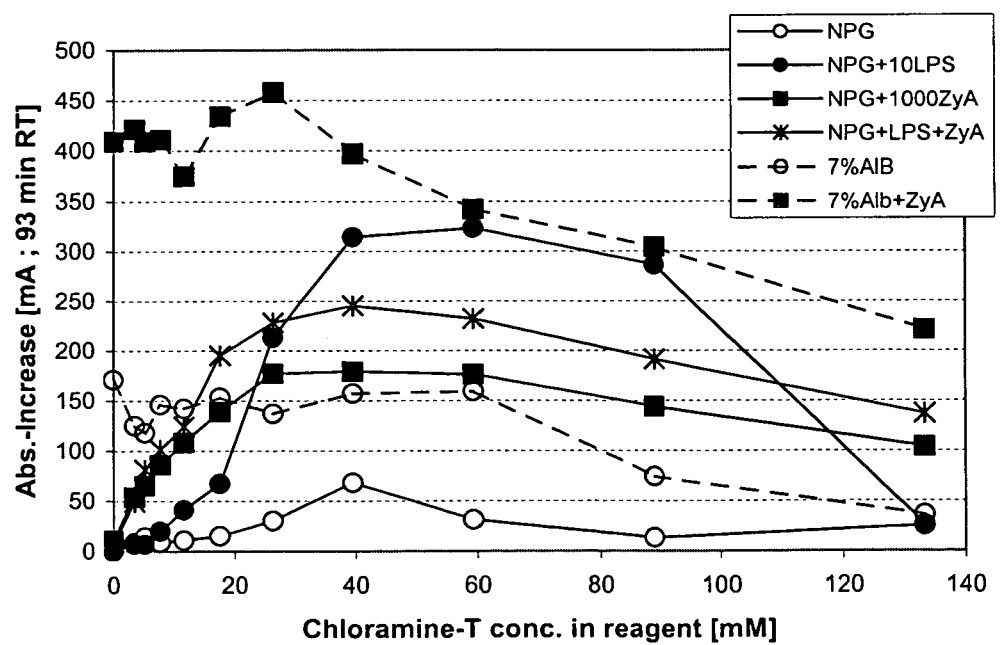

FIG. 16 shows the results of a further invention according to the invention, in which 10 μl 0–133 mmol/l CT in 100 mmol/l NaHCO$_3$, pH 8,5, was incubated for 10 min (37° C.) with 10 μl pooled plasma with normal plasmatic coagulation (NPG) or 7% human albumin (Kabi, Stockholm, Sweden), each of them supplemented with 0 or 10 ng/ml LPS and/or 1000 ng/ml zymosan A (ZyA). Then 50 μl 200 mmol/l methionine and after 3 min at RT 30 μl LAL-reagent Coamatic® were added and delta A was determined after 93 min at RT. The optimal CT concentration in this experiment is about 60 mmol/l.

From FIG. 16 it can be recognized, that for pooled normal plasma, unsupplemented and supplemented with LPS or ZyA, maximal LPS- or glucan-reactivities result, if the oxidant-reagent contains 40–80 mM CT. In the oxidant maximum pooled normal plasma (NPG)+LPS+ZyA has an about 30% lower endotoxin-reactivity than NPG+LPS. Oxidation with >60 mM CT result into a decrease of Limulus-activity of the 7% human albumin-sample, at >60 mM CT ZyA seems to be increasingly destroyed. LPS in plasma is increasingly destroyed by oxidation with >90 mM CT.

Figure 17:
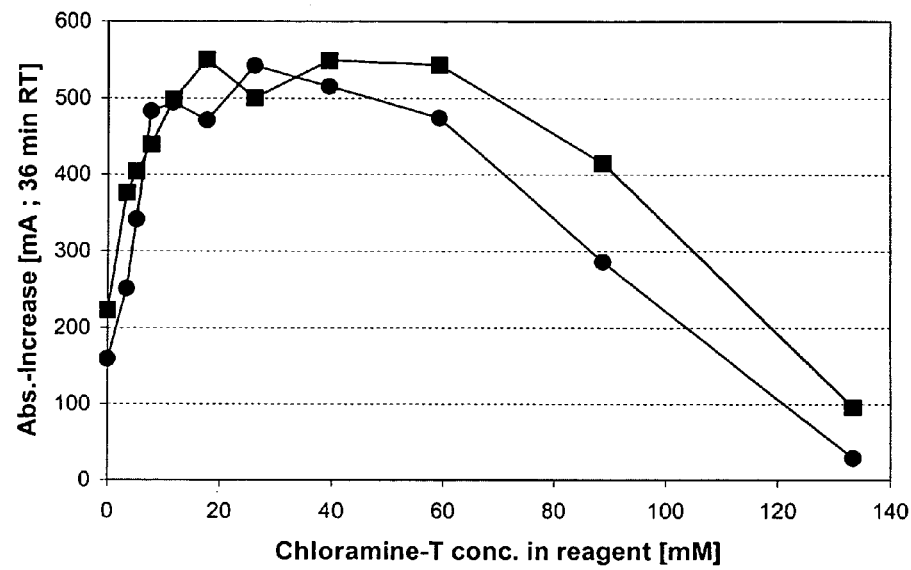

FIG. 17 shows the results of a further procedure according to the invention, in which 10 μl 0–133 mmol/l CT in 100 mmol/l NaHCO₃, pH 8,5 was incubated with 10 μl 7% human albumin supplemented with 10 ng/ml LPS (•) or with 10 ng/ml LPS and 1000 ng/ml Zymosan A (■) for 10 min at 37° C. 50 μl 200 mmol/l methionine was added and after 3 min RT 30 μl LAL-reagent Coamatic® was added and delta A at 405 nm was measured. FIG. 21 shows the results of different CT concentrations, more than 80 mmol/l CT inactivate endotoxin.

From FIG. 17 it is recognized, that maximal LPS-reactivity occurs by oxidation with 20–60 mM CT, that higher oxidant-concentrations result into a diminished LPS-reactivity, and that LPS in albumin sample seems to be increasingly destroyed by oxidation with >80 mM CT.

Figure 18:
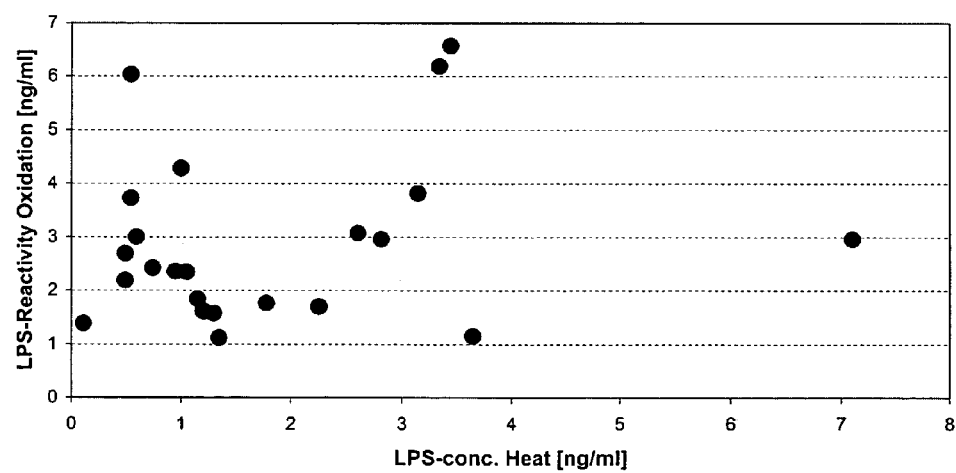

FIG. 18 demonstrates the results of further procedures, in which n=24 unselected EDTA-plasmas of patients were analyzed by means of Coamatic®-LAL test and were treated either with heat (10-fold dilution with H₂O, 15 min at 75° C.) or with 60 mmol/l CT. It is recognized from FIG. 18, that the procedures generate different reactivity results (heat treatment: 1,8 ng/ml LPS+−1,6 ng/ml; CT-treatment: 2,8 ng/ml+−1,6 ng/ml; the correlation factor r=0,210).

Figure 19:
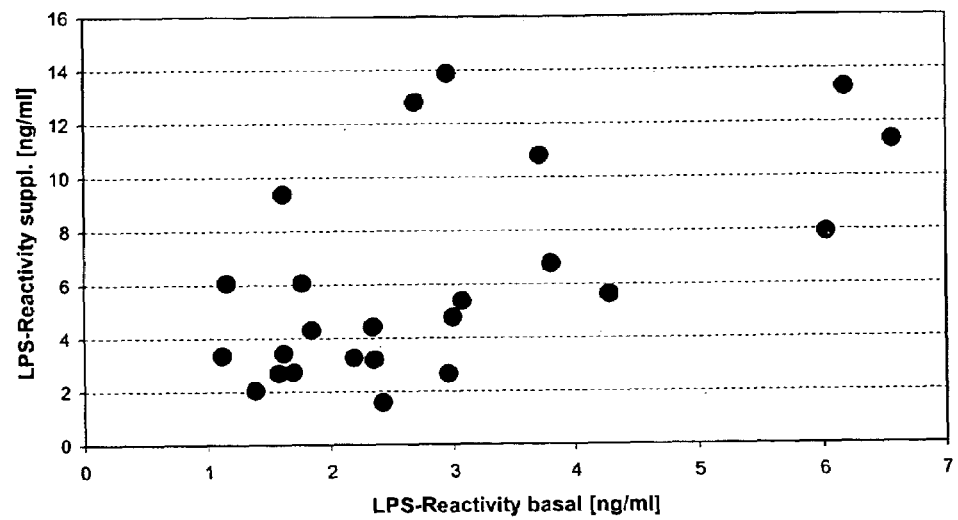

FIG. 19 shows the reactivity-results of further procedures, in which 5 μl 0 or 10 ng/ml LPS were added to the samples and they were tested in the oxidative assay with the Coamatic®-reagent. From before 2,8+−1,6 ng/ml LPS after LPS addition 6,2 ng/ml+−3,8 ng/ml arose, the correlation factor r=0.574.

Figure 20:
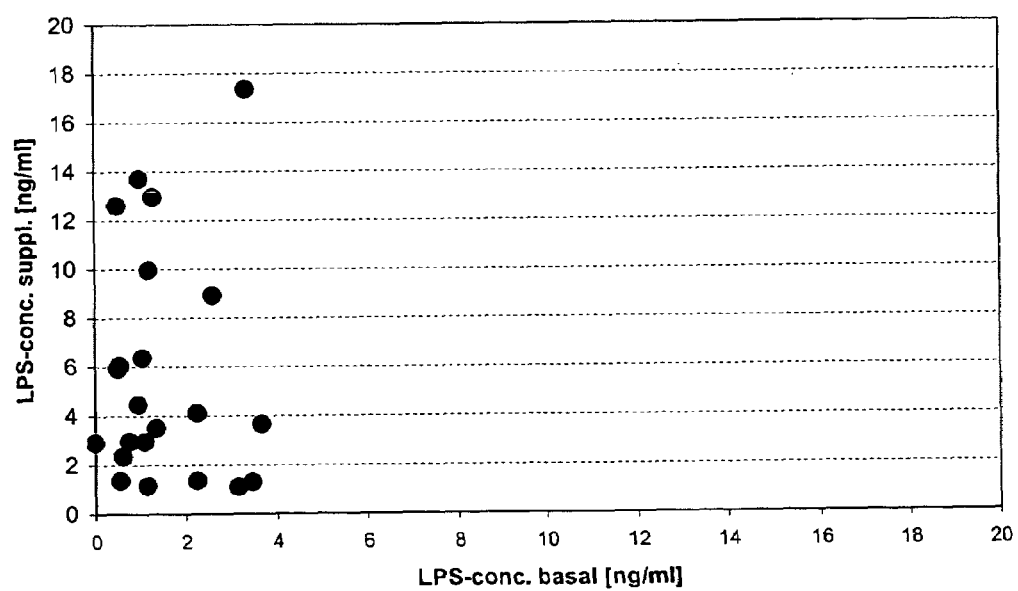

FIG. 20 shows the results of further procedures, in which the addition of 5 μl 10 ng/ml LPS results into 5,8+−4,6 ng/ml LPS after priorly 1,5+−1,1 ng/ml and heat treatment of the samples; the correlation factor is r=0,024. This correlation factor is substantially smaller than that by oxidation of the samples (r=0.574), i.e. there exists an extreme interindividual dispersion in supplementing and regaining of LPS when testing with the (strongly denaturing) heat treatment in contrast to the oxidation method.

FIG. 21 shows the reactivity-results of further procedures, in which 10 μl NPG (pooled from 12 normal plasmas) supplemented with 0–10 ng/ml LPS was incubated with 10 μl 60 mmol/l CT for 10 min at 37° C. Then 10 μl 210 mmol/l ascorbate, 210 mmol/l arginine, pH 8,7, were added. After 3 min at RT 30 μl LAL-reagent (Coatest®, Chromogenix; to be reconstituted in 1,4 ml H₂O; without chromogenic substrate) was added, and after 0–90 min at RT 75 μl 750 mmol/l arginine, pH 8,7, and 30 μl 2 mmol/l Ile-Glu-Gly-Arg-pNA was added and the linear delta A at 405 nm was determined. From FIG. 21 it is recognized, that the optimal time point for linearization in this approach is 45 min RT ist (LPS-calibration curve linear up to 10 ng/ml LPS). FIG. 21 demonstrates, that Limulus-factor-incubation times>60 min RT even result into a decrease of LPS-reactivity (♦,▲). This is due to a self destruction of the Limulus-factors, presence of CS (as in the hyperbolic-rate-assay prior to addition of the linearization reagent) protects before this.

Figure 22:
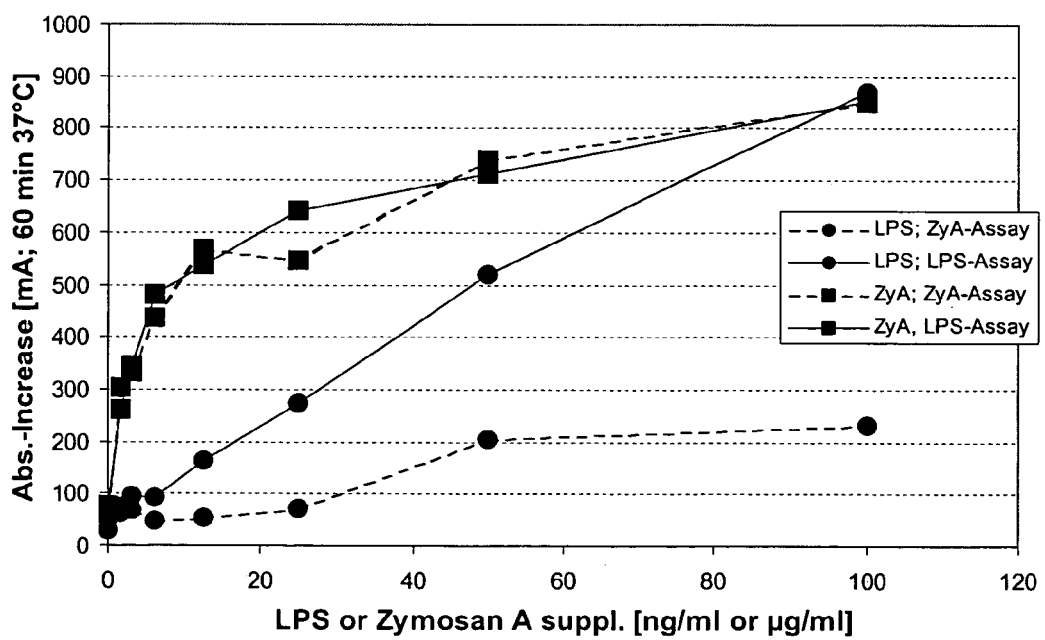

FIG. 22 shows the results of further procedures, in which 10 μl NPG (from 12 normal plasmas) supplemented with 0–100 ng/ml LPS or 0–100 μg/ml zymosan A was incubated with 10 ml 60 mmol/l CT for 10 min at 37° C. Then 10 μl 210 mmol/l arginine, 210 mmol/l ascorbate without (LPS+ glucans) or 2000 U/ml polymyxin B (glucans-test) and 30 μl LAL reagent Coamatic® were added and delta A was determined. FIG. 22 demonstrates, that here a linearity occurs up to 2 μg/ml zymosan A or up to 100 ng/ml LPS. LPS concentrations>40 ng/ml could not be inhibited completely by the used 2000 U/ml polymyxin B.

Figure 23A:
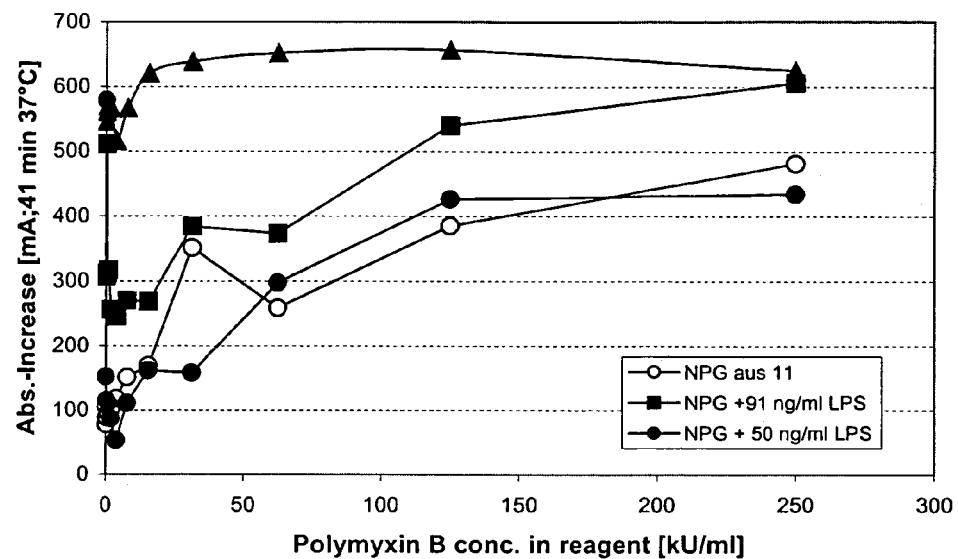
Figure 23B:
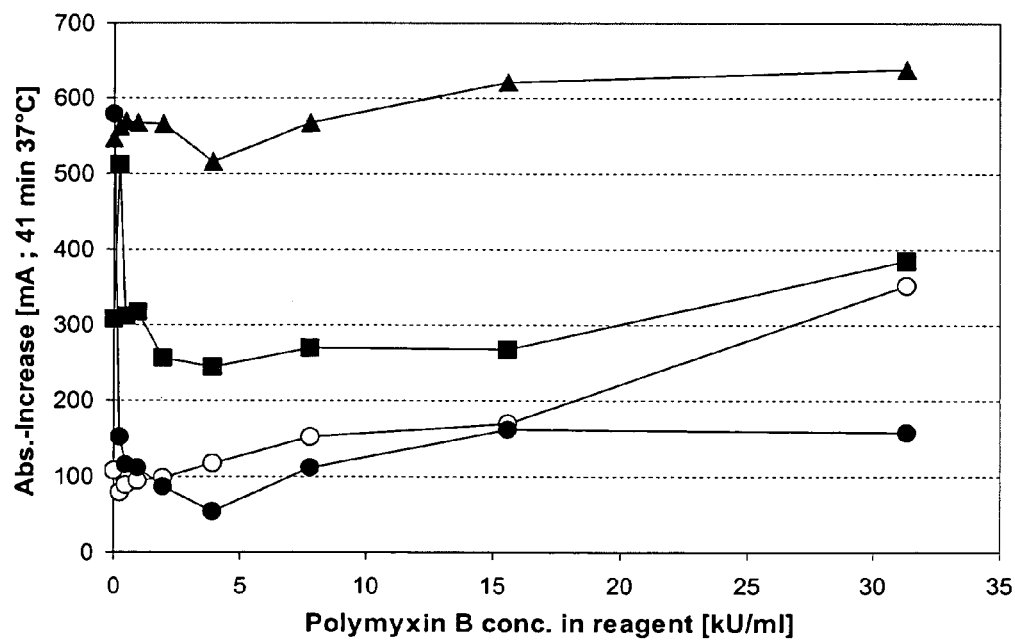
Figure 23C:
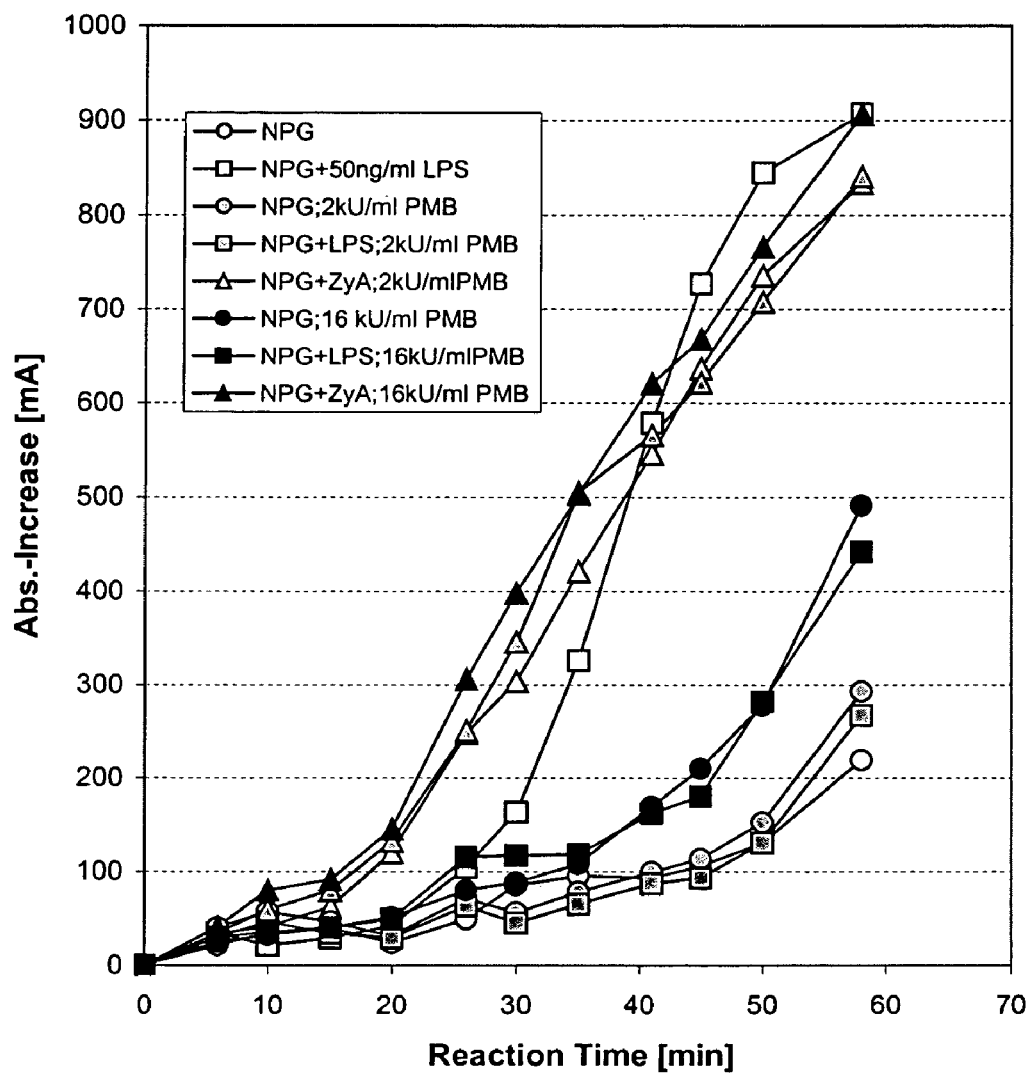

FIGS. 23a–c show the results of further procedures, in which 200 μl NPG, NPG+50 or +91 ng/ml LPS, NPG+50 μg/ml ZyA (Δ) were incubated with 200 μl 60 mmol/l CT in H₂O for 10 min at 37° C. 20 μl thereof was incubated with 10 μl 210 mmol/l arginine, 210 mmol/l ascorbate and 0–250 000 U/ml polymyxin B at 37° C. and delta A was determined. From the FIGS. 23a–c it can be recognized, that polymyxin B itself stimulates the Limulus-system.

FIG. 24 shows a comparison experiment of the procedure according to the state of the art with 75° C. (15 min) treatment of the samples with the procedure according to the present invention with oxidation of the samples with 60 mM chloramine-T® (10 min, 37° C.). Herefore 7.5% human albumin (Kabi, Stockholm, Sweden) basally containing 0.5 μg/ml zymosan A, supplemented with 0–10000 ng/ml LPS (E. coli 0111:B4; purified by gel-filtration; product L 3012: Sigma, Deisenhofen, Germany) or with +0–100 μg/ml zymosan A analyzed as follows:

A. Heat Treatment

Figure 24A:
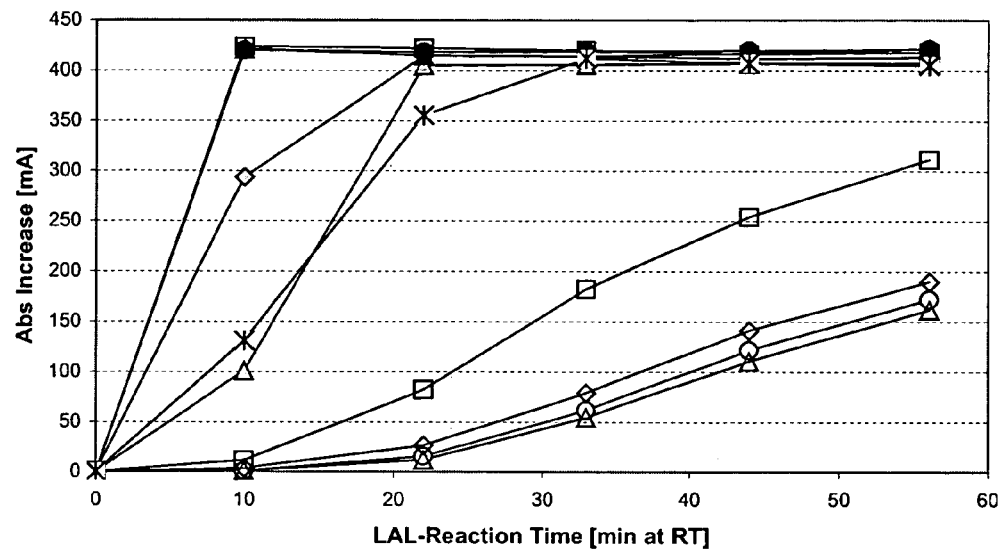
Figure 24B:
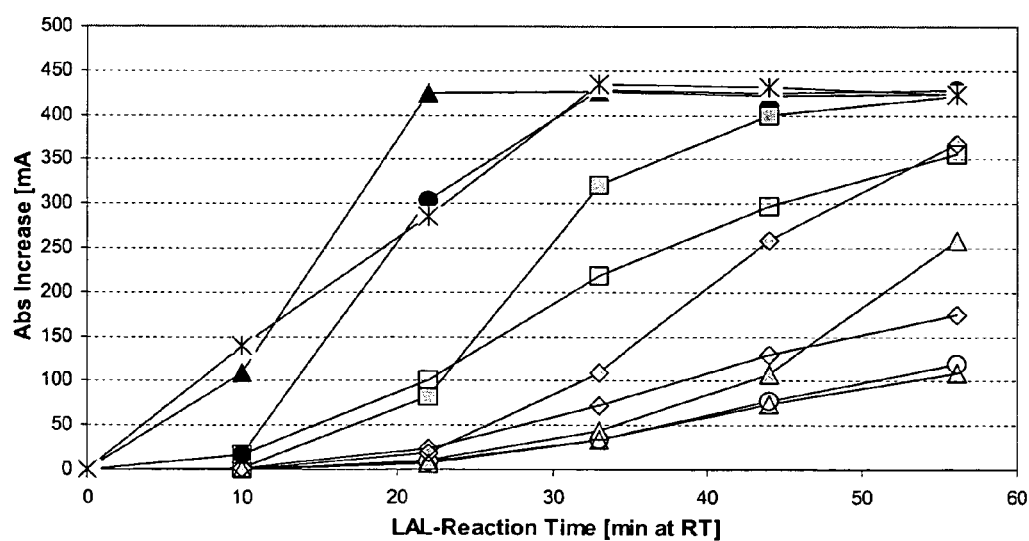
Figure 24C:
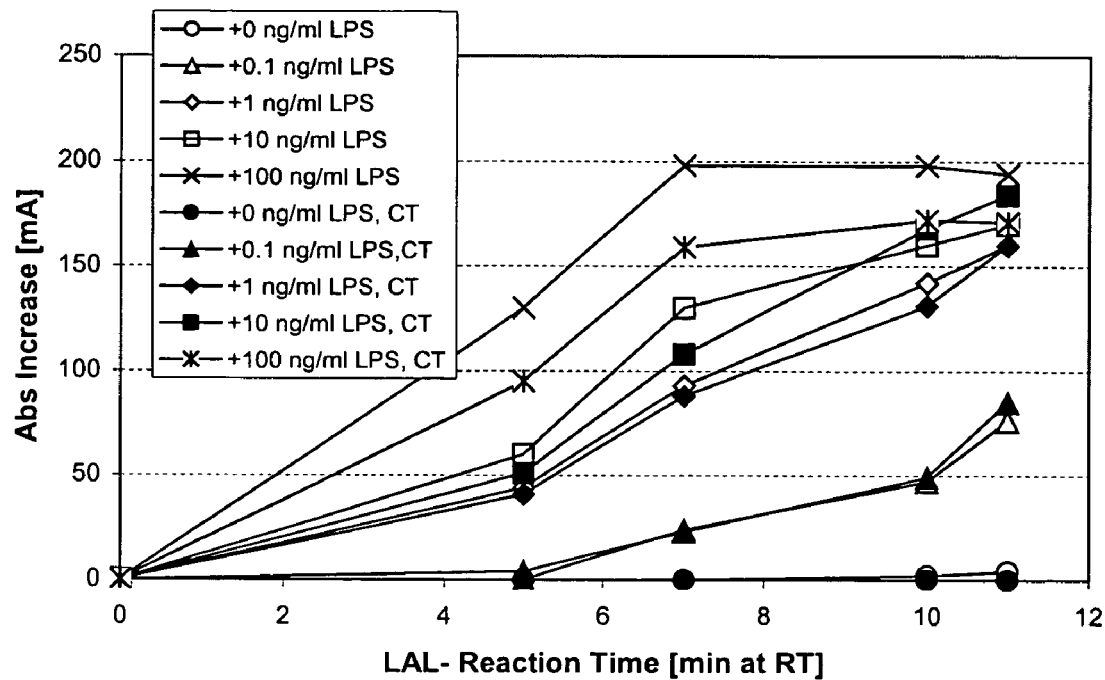

20 μl sample was 10-fold diluted with aqua dest. and incubated for 15 min at RT or at 75° C. (water bath). Then 20 μl heat-treated sample was incubated in duplicate with 20 μl LAL-reagent (Pyrochrome®) at RT and the delta A at 405 nm was determined using a microtiterplate photometer (Milenia-DPC, Los Angeles, USA). +0 ng/ml LPS (○), +0.1 ng/ml LPS (grey Δ), +1 ng/ml LPS (grey ◊), +10 ng/ml LPS (grey □), +100 ng/ml (•), +1000 ng/ml LPS (▲), +0.1 μg/ml ZyA (Δ), +1 μg/ml ZyA (◊), +10 μg/ml ZyA (□), +100 μg/ml ZyA (*). One sees that +1000 ng/ml LPS after heat treatment acts like +0.1 ng/ml LPS at RT (FIG. 24a), i.e. 99.99% of the active LPS were inactivated by the heat treatment (FIG. 24b). Zymosan A is heat resistant.

B. Oxidation Treatment

Figure 24D:
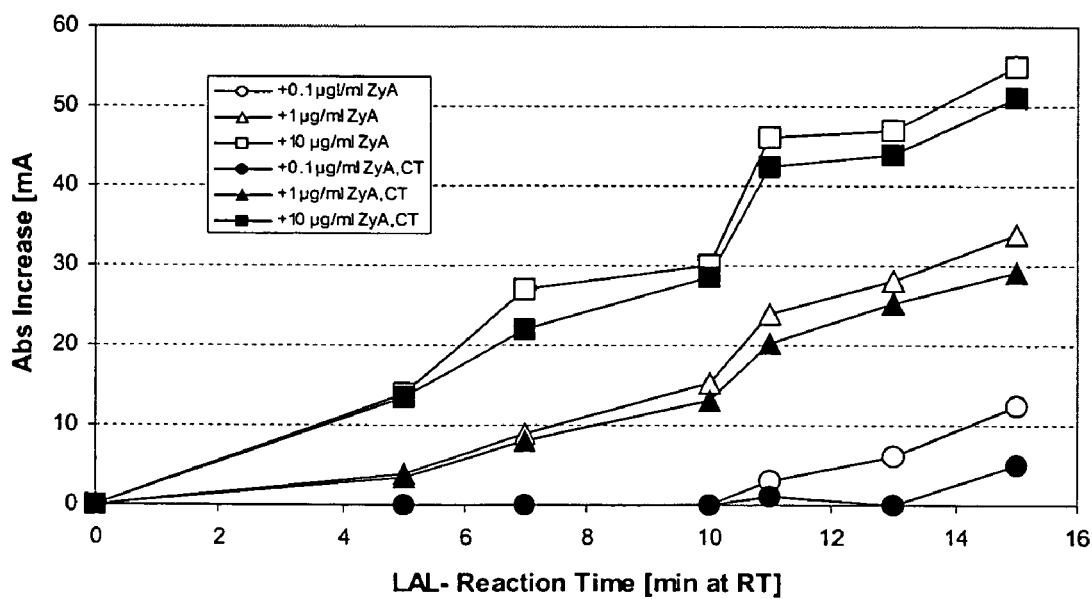

5 μl sample was incubated in duplicate with 5 μl PBS or 60 mM chloramine-T® in PBS for 10 min at 37° C. (water bath). Then 5 μl 230 mM methionine in aqua dest. was added and after 3 min RT 15 μl LAL-reagent (Pyrochrome®) was added and the delta A at 405 nm (RT) was determined. One recognizes that both the LPS-reactivity (FIG. 24c) and the zymosan-reactivity is oxidation resistant (FIG. 24d).

The invention claimed is:

1. A procedure to determine the content of active and/or free lipopolysaccharide, lipid-A and/or glucan in a sample of a biological liquid comprising
    a) treating the sample with at least one oxidant,
    b) adding at least one Limulus amebocyte-factor to the oxidized sample, and
    c) measuring the kinetics of the activation of the at least one Limulus amebocyte-factor that is caused by active and/free lipopolysaccharide, lipid-A and/or glucan,
    wherein the steps a), b) and c) are carried out at a pH between 6 and 10.

2. The procedure according to claim 1, wherein the oxidant is a singlet oxygen generator.

3. The procedure according to claim 1, wherein the oxidant is added to the sample in an amount of 15–200 μmoles per ml sample liquid.

4. The procedure according to claim 1, wherein after the performance of the oxidation any remaining amount of oxidant is inactivated by addition of an antioxidant.

5. The procedure according to claim 1, wherein the activation of at least one factor of the Limulus-system is determined by measuring the amount of chromophore generated by the Limulus-system out of a chromogenic compound that is cleavable by an activated Limulus-factor.

6. The procedure according to claim 1, wherein the biological liquid is selected from the group consisting of blood, blood products, liquor, urine, saliva, bronchoalveolar lavage, ascites, pericardial or pleural effusions, milk, tissues liquids, lymph liquids, and industrially manufactured products that contain anti-*Limulus* factors.

7. The procedure according to claim 1, wherein a heparin containing biological liquid is used that has been supplemented prior to or in the test with at least one heparin inhibitor.

8. The procedure according to claim 1, wherein the biological liquid does not contain heparin or contains up to 1 IU/ml heparin and contains citrate or EDTA.

9. The Procedure according to claim 1, wherein prior to or during the performance of step c) at least one guanidine-compound and/or a chaotropic agent is added to the sample such that the kinetics of the measurement is linear.

10. The procedure according to claim 9, wherein the guanidine-compound is arginine, and the chaotropic agent is an alkali metal cation or an alkaline earth metal cation.

11. The Procedure according to claim 1, wherein the procedure is performed at least twice, once in which a lipopolysaccharide inhibitor is added after step a) and prior to or during step b) and once in the absence of a lipopolysaccharide inhibitor and further comprising determining the difference in the activation of the *Limulus* amebocyte-factor between the two procedures and thereby differentiating reactivity of lipopolysaccharide, lipid-A and glucans and the reactivity of glucans.

12. The procedure according to claim 11, wherein the lipopolysaccharide-inhibitor is polymyxin-B.

13. The procedure according to claim 1, wherein the biological liquid prior to or during step a) is diluted with (human) albumin.

14. The procedure according to claim 1, wherein the biological liquid has a protein concentration of 30–100 g/l.

* * * * *